(12) United States Patent
Koulakis et al.

(10) Patent No.: US 11,389,396 B2
(45) Date of Patent: Jul. 19, 2022

(54) TUMESCENT ANTIBIOTIC INJECTION FOR TREATMENT OF CHRONIC SKIN AND SOFT TISSUE INFECTIONS

(71) Applicant: The Regents of the University of California, Oakland, CA (US)

(72) Inventors: John Koulakis, Porter Ranch, CA (US); Seth J. Putterman, Malibu, CA (US); James C. Dunn, Santa Monica, CA (US); Joshua Rouch, Santa Monica, CA (US); Nhan Huynh, San Jose, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 729 days.

(21) Appl. No.: 16/345,201

(22) PCT Filed: Oct. 30, 2017

(86) PCT No.: PCT/US2017/059093
§ 371 (c)(1),
(2) Date: Apr. 25, 2019

(87) PCT Pub. No.: WO2018/081740
PCT Pub. Date: May 3, 2018

(65) Prior Publication Data
US 2019/0282754 A1    Sep. 19, 2019

Related U.S. Application Data

(60) Provisional application No. 62/414,536, filed on Oct. 28, 2016.

(51) Int. Cl.
| | | |
|---|---|---|
| *A61K 9/00* | (2006.01) | |
| *A61B 17/32* | (2006.01) | |
| *A61M 5/158* | (2006.01) | |
| *A61K 31/00* | (2006.01) | |
| *A61P 17/02* | (2006.01) | |
| *A61P 31/00* | (2006.01) | |
| *A61B 5/055* | (2006.01) | |
| *A61B 6/03* | (2006.01) | |

(52) U.S. Cl.
CPC ............ *A61K 9/0019* (2013.01); *A61B 17/32* (2013.01); *A61K 31/00* (2013.01); *A61M 5/158* (2013.01); *A61P 17/02* (2018.01); *A61P 31/00* (2018.01); *A61B 5/055* (2013.01); *A61B 6/032* (2013.01); *A61B 2017/320004* (2013.01)

(58) Field of Classification Search
CPC ...... A61K 9/0019; A61K 31/00; A61B 17/32; A61B 5/055; A61B 6/032; A61B 2017/320004; A61M 5/158; A61P 17/02; A61P 31/00
See application file for complete search history.

(56) References Cited

U.S. PATENT DOCUMENTS

| | | |
|---|---|---|
| 7,563,223 B2 | 7/2009 | Sampson |
| 2011/0003001 A1 | 1/2011 | Baker |
| 2012/0322783 A1 | 12/2012 | Klein |
| 2015/0182536 A1 | 7/2015 | Klein |
| 2017/0100331 A1 | 4/2017 | Klein et al. |

OTHER PUBLICATIONS

PCT International Search Report & Written Opinion dated Jan. 5, 2018, International Application No. PCT/US2017/059093.

*Primary Examiner* — Robert S Cabral
(74) *Attorney, Agent, or Firm* — Gates & Cooper LLP

(57) ABSTRACT

Methods are taught for treating chronic wounds and skin and soft tissue infections with antibiotic tumescent injection. In such methods, the region of tumescent drug delivery is monitored and expanded by the infusate in order to be 2×-5× larger in area and volume in the region of the wound or infection, the drug in the infusate creates a tissue concentration greater than the MIC in the tumescent volume for selected period of time, and the high concentration has a residence lifetime in the tissue long enough to kill the bacteria. Typically, the methods are performed without the use of vasoconstrictors such as epinephrine and in a manner that avoids physical manipulation of the wound.

20 Claims, 17 Drawing Sheets

TUMESCENT ANTIBIOTIC INJECTION FOR TREATMENT OF CHRONIC SKIN AND SOFT TISSUE INFECTIONS

CROSS-REFERENCE TO RELATED APPLICATIONS

This application claims priority under Section 119(e) from U.S. Provisional Application Ser. No. 62/414,536, filed Oct. 28, 2016, entitled "TUMESCENT ANTIBIOTIC INJECTION FOR TREATMENT OF SKIN AND SOFT TISSUE INFECTIONS", the contents of which are incorporated herein by reference.

TECHNICAL FIELD

This invention relates to the treatment of chronic skin wounds colonized by pathogenic organisms along with the techniques, devices, and instruments used to monitor the wounds and provide proper treatment thereof.

BACKGROUND OF THE INVENTION

Chronic wounds affect over 6.5 million people in the United States at an annual cost of over $25 billion [1]. They are defined as a break in the skin of duration greater than 6 weeks [2] due to a failure of the normal course of acute wound closure, and are almost never seen in patients without complicating factors such as obesity and diabetes that impair their ability to heal [1, 2]. The most common types are venous ulcers, arterial ulcers, diabetic foot ulcers, and pressure ulcers. Attempts to treat chronic wounds have included 1) debridement, 2) dressings of many types, 3) compression bandages, 4) negative pressure devices, 5) topical growth factors, 6) skin grafts, 7) hyperbaric oxygen therapy, and 8) amputation [2, 3, 4].

Direct injections have been used to deliver antimicrobial agents to patients in certain contexts, for example to prevent surgical site infections both in burns [27], 29] and otherwise [49]. In such procedures, solutions containing antibiotics are infused subcutaneously beneath the incision site (before incision) using a method similar to that in tumescent anesthesia. Infection is prevented during surgery because of both the presence of antibiotic, as well as the extra fluid that keeps the tissue hydrated while it is exposed to air. In contrast to tumescent anesthesia, tumescent saphenous vein harvesting, and tumescent prophylaxis, which are in healthy tissue, in direct antibiotic delivery (DAD) the tumescent solution is typically infused underneath and around infections. Certain tumescent methods of antibiotic infusion are described for the treatment of acute wounds (see, e.g. U.S. Pat. No. 9,623,030, and U.S. Patent Publication Nos. 20170216198 and 20170100331). In addition, other tumescent methods include antibiotic infusion in combination with the application of mechanical manipulation in the form of ultrasound (see, e.g. U.S. Pat. No. 8,747,384, and United States Patent Application Publication Nos. 2015/0258320, 2012/0123321 and 2015/0297879). In these methods, antibiotic infusion is performed similarly to that used in tumescent anesthesia (comparable volumes), but the tumescent fluid contains antibiotic.

Chronic wounds are often colonized by pathogenic microorganisms (e.g. antibiotic resistant bacteria) disposed within biofilms, making them particularly difficult to treat. For this reason, there is a need for improved tumescent antibiotic delivery methods that take into account and address the complex physiological microenvironments observed in chronic wounds.

SUMMARY OF THE INVENTION

Chronic wounds colonized by pathogenic microorganisms exhibit a unique microenvironmental physiology, one that inhibits the effectiveness of antimicrobial agents that are effective in other contexts, such as in the treatment of acute wounds. For example, chronic wounds exhibit complex biofilm formation, structures which bond pathogenic microorganisms and colonized tissue matrices within viscous organic hydrogels. The interaction between these biofilms and tissue matrices can create reservoirs where pathogenic organisms within chronic wounds evade therapeutically effective concentrations of antimicrobial agents. The invention disclosed herein provides tumescent infusion methods for treating chronic wounds where fluid amounts and the manner of fluid infusion is carefully monitored in order to break up these reservoirs and deliver therapeutically effective concentrations of antimicrobial agents to the pathogenic microorganisms. Embodiments of the invention further have the benefit of avoiding physical manipulation of the wound, manipulation that has potential to cause tissue damage such as burns and pain in patients. In this way, embodiments of the invention can also be used to decrease the dose or duration of painkillers that are needed to appropriately manage patient pain.

Embodiments of the invention include methods of delivering selected concentrations of antibiotic agents to a chronic wound for a defined amount of time (e.g. at least 2, 3, 4, 5, 10 or more hours). These methods comprise administering a solution comprising the antibiotic agent via tumescent injection to regions of tissue colonized by pathogenic microorganisms. In these methods, the amount of solution administered is monitored by health care professionals to be sufficient to expand the volume of the region of colonized tissue between 2 and 5 fold so as to create an edema on a skin surface that expands extracellular matrices throughout the colonized tissue. In these methods, the amount of infused fluid, the rate of infusion and the composition of the antibiotic solution is monitored so that the concentration of the antibiotic agent within the tissue that has been expanded is above a minimum inhibitory concentration for the pathogenic microorganism for at least 4 hours. In addition, in these methods, the antibiotic solution is administered so as to generate a hydraulic conductivity throughout the colonized tissue that is at least 10 times greater than the hydraulic conductivity in tissue that has not been expanded. Finally, in these methods, the antibiotic solution is administered at a rate selected to form an observable boundary between the tissue that has been expanded and the tissue that has not been expanded, and the administration of the antibiotic solution is monitored so that the observable boundary occurs in uncolonized tissue and is at least 1 centimeter away on the skin surface from the region of colonized tissue. Given the knowledge of the efficacy associated with dense drug dispersal and multi-hour residence time in situ, embodiments of the invention can be used to effectively treat otherwise untreatable wounds by keeping drug concentrations above minimum inhibitory levels for extended periods of time. The tumescent infusion methods disclosed herein are therefore useful for treating chronic wounds in humans as well as in a variety of other animals such as horses, cows, cats, dogs, goats and the like.

As discussed in detail below, embodiments of the invention include methods of delivering an antibiotic agent to a chronic wound having a region of tissue colonized by a pathogenic microorganism in a manner that selectively modulates the diffusion of the agent(s) delivered in vivo. These methods comprise administering a solution comprising the antibiotic agent via tumescent injection to the region of colonized tissue, wherein the volume of the solution is selected and monitored so that the volume of antibiotic solution administered is sufficient to expand the area of the colonized tissue between 2 and 5 fold so as to create an edema on a skin surface that expands extracellular matrices of colonized tissue throughout the colonized tissue, and the antibiotic solution is further administered in a manner selected to generate an apparent diffusion coefficient at that is greater than 90% of the value for bulk water ($2.5 \times 10^{-3}$ mm$^2$ s$^{-1}$ at 40 C) throughout the tissue that has been expanded.

In typical embodiments of the invention, an observable tumescent infusion boundary created by the methods disclosed herein is located at a region where the hydraulic conductivity changes at least one order of magnitude between the tissue that has been expanded and the tissue that has not been expanded and the administration of the antibiotic solution is monitored so that the boundary occurs in uncolonized tissue and is at least 1 centimeter away on the skin surface from the region of colonized tissue. In certain embodiments of the invention, the boundary is observed by the naked eye and/or at least one further technique selected from 3-D scanning, computed tomography (CT), diffusion-weighted magnetic resonance imaging (DW-MRI), and poroviscoelastic relaxation. Typically, these methods are performed on chronic wounds without the use of vasoconstrictors such as epinephrine and/or are performed in a manner that avoids application of mechanical stimulation to the colonized tissue.

Embodiments of the invention include methods of treating a chronic wound colonized by a pathogenic microorganism that include first debriding the wound to remove non-viable tissue and expose a layer of granulation tissue. These methods then include delivering an antibiotic agent to regions of colonized tissue in the chronic wound by administering a solution comprising the antibiotic agent via tumescent injection to the regions of colonized tissue. In these methods, the amount of solution administered is selected to be sufficient to expand the volume of the regions of colonized tissue between 2 and 5 fold so as to create an edema on a skin surface that expands extracellular matrices throughout the colonized tissue, the antibiotic solution is administered so that the concentration of the antibiotic agent within the tissue that has been expanded is above a minimum inhibitory concentration for the pathogenic microorganism for at least 4 hours, the antibiotic solution is administered so as to generate a hydraulic conductivity throughout the colonized tissue that is at least 10 times greater than the hydraulic conductivity in tissue that has not been expanded, the antibiotic solution is administered at a rate selected to form an observable boundary between the tissue that has been expanded and the tissue that has not been expanded, and the administration of the antibiotic solution is monitored so that the observable boundary occurs in uncolonized tissue and is at least 1 centimeter away on the skin surface from the region of colonized tissue. These methods then comprise applying a skin graft to the debrided tissue following the tumescent methodology disclosed herein.

Embodiments of the invention can be used to treat a wide variety of chronic wounds including venous ulcers, arterial ulcers, diabetic ulcers, and pressure ulcers etc. Embodiments of the invention can be used in hospitals and veterinary clinics, wound care centers, geriatric homes, outpatient centers, in-home doctor visits, etc. to treat wounds that have failed to heal on their own, may be unresponsive to previous medical care, may be infected with antibiotic resistant bacteria, may be ischemic, and/or may have poor circulation. The procedure will shorten the extent and/or lifetime of the wound; prevent or reverse the spread of infections, necrotizing fasciitis, gangrene and/or other complications; and prevent amputations of extremities. Practitioners may utilize instruments or devices that will be developed to characterize the wound and surrounding tissue before and/or after the procedure and give feedback to the practitioner regarding the sufficiency, adequacy, and/or extent of treatment to assist him/her in fully and properly treating the affected areas.

Embodiments of the invention have the ability to achieve high antibiotic concentrations directly in skin and soft tissue infections for sufficient time to kill bacteria. Simultaneously, total antibiotic doses can be kept low, minimizing systemic toxicity. In particular, even antibiotic resistant strains of pathogenic microorganisms can be killed in this way because of the high local concentration of antimicrobial agent. The infusion can be performed in bodily regions with reduced or poor circulation that limit the ability of systemically delivered drugs. In fact, the residence time of tumescent injections in tissue with poor circulation may be longer, facilitating treatment. Antibiotics that have been ineffective at treating resistant infections with systemic dosage can be used effectively with localized delivery, extending the usable lifetime of already-developed antibiotics. This technique achieves results on difficult, otherwise untreatable wounds, with a small number of applications. After being tumesced, subcutaneous tissue returns to normal as the tumescence goes away, without long-term adverse effects. Effective treatments for chronic wounds will save patients from pain and amputations and allow them to return to a normal way-of-life. In addition, such treatments have the potential to save families from tremendous emotional and financial burdens, and reduce national health care expenditure by billions annually.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Figure 1:
FIG. 1: Blue-dyed saline is injected into the subcutaneous tissue of a dead, adolescent Yucatan pig. The injected fluid expands the tissue matrix, and is trapped in a gel or jelly-like state. Upon cutting into the tumescence, the liquid does not run out, but is held in place.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

This application references a number of different publications as indicated throughout the specification by reference numbers enclosed in brackets, e.g., [x]. A list of these different publications ordered according to these reference numbers can be found below in the section entitled "REFERENCES". All publications, patents, and patent applications cited herein are hereby incorporated by reference in their entirety for all purposes.

Chronic wounds are by definition those which have not responded to traditional therapy and last for prolonged lengths of time. The most common types fall in to four categories: Diabetic ulcers, pressure ulcers, venous ulcers, and arterial ulcers. Chronic wounds colonized by pathogenic microorganisms exhibit a unique microenvironmental physiology. Persistent, runaway inflammation is one hallmark of most chronic wounds (see, e.g. R. F. Diegelmann Wound Repair Regen, vol. 11, pp. 490-495, 2003 and M. A. Loots et al., J. Invest. Dermatol., vol. 111, pp. 850-857, 1998). Growth factors, cytokines, immune cells, and other healing mediators are locked in an imbalanced state that prevents healing (see, e.g. R. Zhao et al., International Journal of Molecular Sciences, vol. 17, no. 2085, pp. 1-14, 2016 and T. Velnar et al., The Journal of International Medical Research, vol. 37, no. 5, pp. 1528-1542, 2009). Generally, chronic wounds mainly form in locations where circulation is already poor, for example from diabetes, atherosclerosis, obesity, or other mechanisms. Prolonged attempts of wound closure lead to fibrin cuffs, surrounding capillaries that hinder the flow of oxygen, nutrients, healing mediators, and cell migration to proximal tissue (see, e.g. N. L. Browse et al., The Lancet, vol. 2, no. 8292, pp. 243-246, 1982, K. G. Burnand et al., British Medical Journal, vol. 285, pp. 1071-1072, 1982, and J. J. Bergan et al., The New England Journal of Medicine, vol. 355, no. 5, p. 488, 2006). Infections, often resistant to antibiotics, contribute to the non-healing of wounds.

Complicating factors in the treatment of chronic wounds include the presence of biofilms, which are present in 60% of chronic wounds, but only 10% of acute wounds (see, e.g. G. A. James et al., Wound Repair and Regen., vol. 16, no. 1, pp. 37-44, 2008). When the bacterial density in a wound exceeds a threshold, individual (planktonic and mobile) bacteria form polymicrobial colonies and begin to act collectively (see, e.g. A. Clinton et al., Lab Medicine, vol. 46, no. 4, pp. 277-282, 2015). Bacteria sense that their density has reached critical through a phenomenon called quorum sensing, and begin to express different genes. They excrete exo-polymeric substance, which forms a gel-like network (the biofilm) to house the microbes. The biofilm contains structures such as water channels and mushroom towers that bring in nutrients and carry away waste, and provides a barrier to antimicrobial agents and immune cells. Microbes in the biofilm become sessile and reduce their metabolism, which reduces their susceptibility to antibiotics.

The invention is a procedure designed specifically for the treatment of chronic wounds whereby a solution containing a high concentration of antibiotic is infused tumescently into healthy tissue beneath and peripheral to an infected skin or soft tissue infection, and the infected tissue itself. In these methods, the injection technique and volume of liquid injected is monitored such that that the entire wound bed, and to some extent all surrounding healthy tissue, swells approximately uniformly. The tissue must be densely filled with solution—i.e. no empty spots. The total antibiotic dose, the antibiotic concentration in the tumescent fluid, and the total volume injected (degree of swelling) are chosen so that 1) the total dose is safe for the patient, 2) the extent (in area) of the tumescence completely covers the wound, 3) the antibiotic concentration in the solution is higher (with a safety factor) than the minimum inhibitory concentration (MIC) of any bacteria present in the wound, 4) the antibiotic concentration remains above MIC for a period of time long enough (e.g. several division times in the case of bacteriostatic antibiotics) to kill any bacteria present. The timescale that the antibiotic concentration remains localized in the tumesced area is, to a large degree, determined by the level of tumescent swelling.

This invention was enabled by our discrediting of aspects of common medical wisdom and synthesis of existing techniques. One barrier was the understanding that infusing fluid into infections spreads the infection [6, 18]. Although this may be true when the fluid does not contain antibiotics, it is not necessarily true when it does. A second misunderstanding is that ultrasound enhances fluid diffusion in gels [58, 59]. A third misunderstanding comes from the subeschar antibiotic clysis literature, where studies on rats show that subeschar infusions have no benefit compared to infusions away from the wound [32], pointing research astray. It is known that rat skin is anatomically different than human skin and that pig skin is a better match [60]. The looser skin of rats does not keep the injection contained and it is therefore not much different than systemic dose. We combine insight from subcutaneous antibiotic delivery, where pharmacokinetic curves show that a "depot" of drug continues to supply serum levels for an extended time; subeschar antibiotic clysis, where low-volume, non-tumescent/edematous, continuous direct infusions help fight already established infections in tissue with poor circulation; and tumescent anesthesia, where high volume injections expand subcutaneous tissue and remain locked in the tissue for many hours. Tumescent antibiotic injections keep high concentrations of antibiotic directly in the region in which it is needed for several hours.

Embodiments of the invention disclosed herein are designed to overcome limitations of other tumescent infusion methodologies such as those disclosed by Klein (see, e.g. U.S. Pat. No. 9,623,030, and U.S. Patent Publication Nos. 20170216198 and 20170100331). For example, embodiments of the invention are designed for the treatment of chronic wounds, wounds which differ substantially from acute wounds that are disclosed by Klein (and which therefore require different considerations). In particular, Klein does not disclose any treatment for chronic wounds (much less one having the constellation of elements found in the invention disclosed herein) because they are fundamentally different from the acute wounds. Studies on how chronic wounds differ from acute wounds include Zhao et al., International Journal of Molecular Sciences 17(12) 2016 and Demidova-Rice et al., Advances in Skin & Wound Care 25 (7) 2012. Key features of chronic wounds include excessive inflammation, matrix degradation, impaired angiogenesis, extracellular matrix degradation, that happen as a result of 1) poor perfusion, 2) insufficient metabolism and nutrition, 3) elevated pressure, 4) infection, 5) necrosis.

Embodiments of the invention overcome limitations of other tumescent infusion methodologies such as those disclosed by Silberg (see, e.g. U.S. Pat. No. 8,747,384, and United States Patent Application Publication Nos. 2015/0258320, 2012/0123321 and 2015/0297879). For example, Silberg directs artisans to use tumescent infusion methodologies in combination with the application of ultrasound. In these methods, the application of around 1 MHz, 3 W/cm$^2$ ultrasound over the tumesced region is claimed to disperse antibiotic within the subcutaneous tissue [53, 54]. However, our studies have surprisingly shown that therapeutic ultrasound is not effective at accelerating tumescence dispersal (e.g. dispersing antibiotic agents disposed in tumescent fluids). For this reason, embodiments of the invention are designed to avoid physical manipulation of the wound (e.g. massage and ultrasound), because, for example, this manipulation has the potential to cause tissue damage and pain in patients. For example, in certain contexts, the application of ultrasound can cause tissue damage such as burns (see, e.g. Olivecrona et al., BMC Cardiovasc Disord (2005) 5: 8 and Mancia et al., (2016). Predicting Tissue Susceptibility to Mechanical Cavitation Damage in Therapeutic Ultrasound. Ultrasound in Medicine and Biology. DOI: 10.1016/j.ultrasmedbio.2017.02.020). By avoiding physical manipulation of the wound, embodiments of the invention can therefore be used to decrease tissue damage and/or the dose or duration of painkillers that are needed to appropriately manage patient pain following a treatment procedure.

Embodiments of the invention include methods of administering a solution comprising the antibiotic agent via tumescent injection to the region of colonized tissue in a manner that modulates macromolecular diffusion in the wound as can be inferred though changes in hydraulic conductivity. Hydraulic conductivity (or permeability) is a measure of the resistance to fluid flow through the subcutaneous tissue and is strongly affected by the interstitial matrix which is the porous geometry of the tissue. The parameter typically cited is 'k' which relates to the narrowness and extent of channels permeated by fluid. This 'k' is a proportionality constant that relates the flow rate to a pressure gradient, as in Darcy's law. This is the key parameter which can increase by a factor of $10^5$ from normal tissue to expanded tissue. When this parameter is increased then it is possible for larger molecules than water such as antibiotics [1 kilodalton], bodily proteins, and immune cells, to permeate the colonized region easier. Methods for observing and characterizing phenomena such as tissue fluid mobility, hydraulic conductivity, diffusion, perfusion and the like are well known in the art and described for example in Guyton et al., Circulation Research, vol. 19, no. 2, pp. 412-419, 1966, Bihan et al., Radiology. 1986 November; 161(2):401-7, Bihan et al., Radiology. 1988 August; 168(2):497-505, Swabb et al., Cancer Res. 1974 October; 34(10):2814-22, Jackson et al., Biorheology 19; 317-330, 1982, Netti et al., AICHE Journal, 49(6), 1580-1596, Guyton, Circulation Research. 1965; 16:452-460, Koh et al., AJR 2007; 188:1622-1635 and Chary et al., Proc Natl Acad Sci USA. 1989 July; 86(14): 5385-9.

In embodiments of the invention, mechanisms fundamental to chronic wound colonization processes are physically and chemically disrupted. Mechanical structures in biofilms are destroyed (if not removed by debridement) by the forced expansion of the underlying interstitial matrix foundation. The average inter-bacterial distance is increased and concentrations of mediators needed for quorum sensing drop via the very specific dilution/flushing methodologies disclosed herein. Bacteria are encouraged to revert back to their planktonic state, rendering them more vulnerable to antibiotics. This multifaceted attack on their structure, quorum sensing, and sessile nature in combination with the modulation of diffusion in the wound and a permeating high concentration antibiotic decimates biofilms that are characteristic of chronic wounds.

In an exemplary embodiment of the invention, tumescent antibiotic injection is used on localized skin infections. A culture of the infection is taken to identify the offending organism and an effective antibiotic is identified. The antibiotic is diluted into a volume of physiological saline or other isotonic fluid that is chosen to be large enough to cover the infected wound area and cause sufficient expansion/tumescence to keep the antibiotic localized for multiple bacterial doubling times. Vasoconstricting drugs such as epinephrine may (or may not) be used to increase the localization time. After anesthetizing the patient, the wound can be debrided until healthy, well-vascularized tissue is visible on the entire wound bed and periphery. Antibiotic solution is infused as with the "tumescent anesthesia" protocol; a cannula is inserted through one or more incisions and fluid is injected underneath and circumscribing the wound in such a way to achieve uniform tumescence. Optionally, a skin graft may then be applied to cover the wound. The wound should remain immobilized post-operatively to allow the infusion to remain localized as long as possible. Repeated tumescent injections, or a continuous infusion into the tumescence with an IV, may be performed to keep the drug concentration high for a longer period of time.

In typical embodiments of the invention, the amount of solution administered and rate of infusion is selected to be sufficient to expand the volume of the region of colonized tissue at least 2, 3, 4 or 5-fold, so as to create an edema on a skin surface that expands extracellular matrices throughout the colonized tissue. In such methods, the antibiotic solution is administered so that the concentration of the antibiotic agent within the tissue that has been expanded is above a minimum inhibitory concentration for the pathogenic microorganism for a defined period of time, such as at least 4, 6, 8, 10, 12 or more hours. In addition, in these methods the antibiotic solution is administered so as to generate a hydraulic conductivity throughout the colonized tissue that is at least 10 times greater than the hydraulic conductivity in tissue that has not been expanded, and the antibiotic solution is administered at a rate selected to form an observable boundary between the tissue that has been expanded and the tissue that has not been expanded. The administration of the antibiotic solution is monitored so that the observable boundary occurs in uncolonized tissue and is at least 1 centimeter away on the skin surface from the region of colonized tissue. Computed tomography studies designed to monitor the spread of molecules in the region of infusion (studies which used an iodine contrast agent that is about the same size as the antibiotic agent cefazolin) show that, along with water molecules, antibiotic agents will have an enhanced dispersion throughout this region due to the higher hydraulic conductivity. In this context, a wide variety of antibiotic agents can be used with these methods (e.g. cephalosporins, trimethoprim-sulfamethoxazoles, tetracyclines, doxycyclines/minocyclines, linezolid etc.). Optionally, the antibiotic solution is administered so that the concentration of the antibiotic agent within the tissue that has been expanded is at least 2, 4 or 6 times a minimum inhibitory concentration for the pathogenic microorganism for at least 4 hours.

Typically, these methods are performed on chronic wounds in the absence of the application of a vasoconstrictor (e.g. epinephrine) to the colonized tissue in order to, for example avoid inhibiting already poor circulation. Moreover, we have shown that even in healthy tissue the antibiotic solution resides long enough to stop the infection in the absence of vasoconstrictors. So by employing such embodiments in unhealthy tissue, drugs such as antimicrobial agents will reside longer and do their job without the need for agents such as epinephrine which in the end maybe counter useful for the treatment of chronic wounds.

Typically, the antibiotic solution is administered in a plurality of infusions so that the concentration of the antibiotic agent within the tissue that has been expanded is above a minimum inhibitory concentration for the pathogenic microorganism for at least 4 hours. A wide variety of pathogenic organism can be treated in this way (e.g. *Staphylococcus aureus*/MRSA, *Streptococcus pyogenes*, Enterococci, *Pseudomonas aeruginosa* and the like). In some embodiments of the invention, the pathogenic microorganism colonizing the chronic wound is resistant to antibiotic agents administered systemically. In certain embodiments of the invention, the boundary is observed by the naked eye and at least one further technique selected from 3-D scanning, computed tomography (CT), diffusion-weighted magnetic resonance imaging (DW-MRI), and poroviscoelastic relaxation.

In embodiments of the invention, the observable boundary of tumescent infusion is located at a region where the hydraulic conductivity changes at least one order of magnitude between the tissue that has been expanded and the tissue that has not been expanded and the administration of the antibiotic solution is monitored so that the boundary occurs in uncolonized tissue and is at least 1 centimeter away on the skin surface from the region of colonized tissue. In certain embodiments of the invention, the amount of solution administered is selected to generate an apparent diffusion coefficient throughout the tissue that has been expanded that is greater than 90% of the value for bulk water ($2.5 \times 10^{-3}$ mm$^2$ s$^{-1}$ at 40 C). Apparent diffusion coefficient is typically derived from observations using magnetic resonance imaging and is the diffusion as modified by both the presence of the interstitial matrix and the take up and release from the circulatory system that permeates the tissue. Note that when tissue is expanded the percentage of tissue that is made up of capillaries is diminished. The bulk diffusion coefficient of water is the diffusion of water when there are no boundaries restricting its flow.

Other embodiments of the invention include methods of treating a chronic wound colonized by a pathogenic microorganism that include first debriding the wound to remove non-viable tissue and expose a layer of granulation tissue. These methods then include delivering an antibiotic agent to regions of colonized tissue in the chronic wound, the method comprising administering a solution comprising the antibiotic agent via tumescent injection to the regions of colonized tissue. In these methods, the amount of solution administered is selected to be sufficient to expand the volume of the regions of colonized tissue between 2 and 5 fold so as to create an edema on a skin surface that expands extracellular matrices throughout the colonized tissue, the antibiotic solution is administered so that the concentration of the antibiotic agent within the tissue that has been expanded is above a minimum inhibitory concentration for the pathogenic microorganism for at least 4 hours, the antibiotic solution is administered so as to generate a hydraulic conductivity throughout the colonized tissue that is at least 10 times greater than the hydraulic conductivity in tissue that has not been expanded, the antibiotic solution is administered at a rate selected to form an observable boundary between the tissue that has been expanded and the tissue that has not been expanded, and the administration of the antibiotic solution is monitored so that the observable boundary occurs in uncolonized tissue and is at least 1 centimeter away on the skin surface from the region of colonized tissue. These methods then comprise applying a skin graft to the debrided tissue following tumescent injection of the antibiotic agent. Optionally the method is performed in the absence of the application of a vasoconstrictor to the colonized tissue and/or the tumescent injection is performed in a manner that avoids application of mechanical stimulation to the tissue expanded by the antibiotic solution.

In typical embodiments of the invention, the boundary of infused antibiotic solution is observed by the naked eye and at least one further technique selected from 3-D scanning, computed tomography (CT), diffusion-weighted magnetic resonance imaging (DW-MRI), and poroviscoelastic relaxation. Optionally, the solution is formulated to include additional agents such as an imaging agent that facilitates observation of the area of colonized tissue that has been expanded between 2 and 5-fold. Alternatively, the solution is formulated to further include an agent selected to interfere with or otherwise modulate the inflammation cycle (e.g. a steroidal agent). Optionally, the chronic wound is a venous ulcer, an arterial ulcer, a diabetic foot ulcer, or a pressure ulcer. Wounds of this type that are good candidates for the procedure described herein are localized in extent, covering area about 50 in$^2$ or smaller. Larger wounds may be treated. The smaller the extent, the higher the antibiotic concentration that can be achieved in the wound without reaching systemic toxicity. They are preferably confined to subcutaneous tissue, and have some amount of healthy tissue beneath and circumscribing them.

Figure 17:
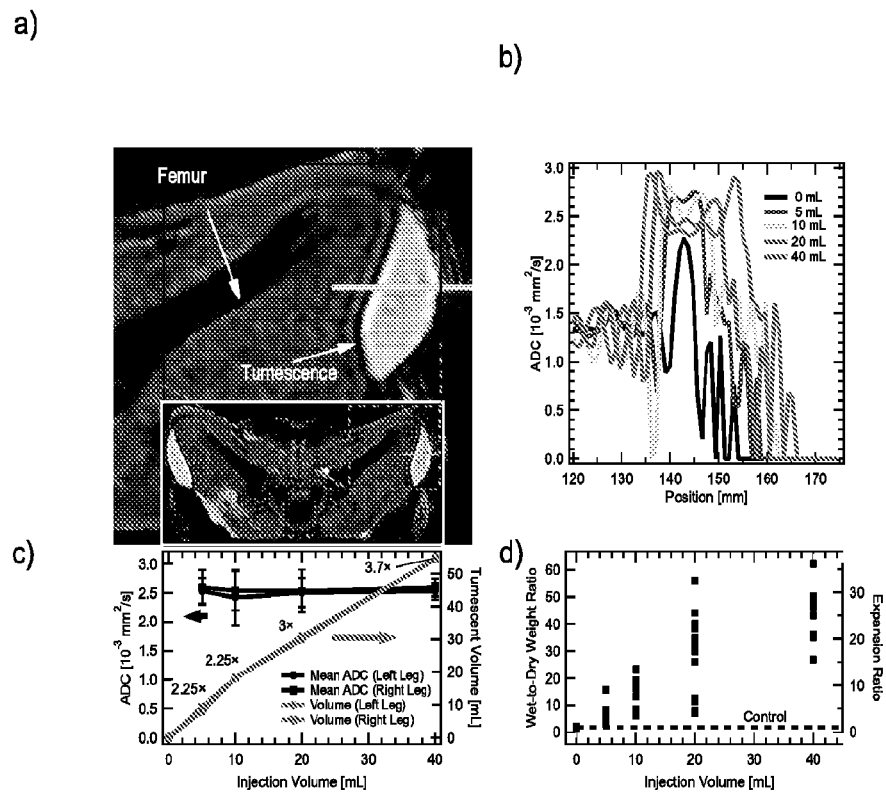
FIG. 17: Expansion of tumescent tissue characterized by Diffusion-Weighted MRI. Panel a) is an apparent diffusion coefficient (ADC) map showing an axial cross section through the quadriceps of an adolescent Yucatan pig laying on its back after 40 mL physiological saline had been infused into the subcutaneous tissue of both right and left thighs. Whiter regions correspond to higher ADC. Lineouts along the green line in a) are shown in b), as more liquid is infused into the subcutaneous tissue. The tumescent volume and spatially averaged ADC are plotted in c). Uncertainty bars on the mean ADC plot indicate the standard deviation of the ADC within the tumescent volume. Numbers next to volume curve markers are the average expansion ratio as calculated from the tumescence volume. Expansion of subcutaneous tissue can also be measured by surgically removing samples from within it, and weighing them before and after desiccation. Tumescent tissue samples were chosen to represent maximal levels of expansion (as in the bluer regions of FIG. 16a)—they are not randomly selected. The wet-to-dry weight ratio, and expansion ratio, are plotted in d). The scatter of the points with the same injection volume is characteristic of the spatial variations within each tumescence.

As noted above, diffusion-weighted magnetic resonance imaging (DW-MRI) is a non-invasive method of monitoring the tumescent infusion and measuring the apparent diffusion coefficient (ADC)—a measure of the molecular diffusion of water within tissue. In an example of this, we infused increasing volumes of saline (0-40 mL) into both right and left thighs of an anesthetized juvenile Yucatan pig, and DW-MRI was performed to quantify the tumescent size and mean ADC as a function of total volume infused. FIG. 17A is an axial, ADC map intersecting the tumescence after 40 mL was infused. The ADC is about $1.4 \times 10^{-3}$ mm$^2$ s$^{-1}$ in the muscle underneath the tumescence, as seen in lineouts crossing the tumescence (FIG. 17B). We expected the ADC within the tumescence to increase progressively as larger volumes of saline were infused. Amazingly however, the ADC saturates at a value consistent with the self-diffusion coefficient of water for even the smallest injection performed, 5 mL. It appears that even for such small injections, the tissue has unexpectedly expanded enough where the structure of the interstitial matrix negligibly restricts molecular diffusion. As more fluid is infused, the tumescence expands both into the empty space above the skin, but also into the body below; a small volume of normal, unexpanded tissue swells to a larger volume. In addition to the thickness growing, the area covered broadens as well. We define the average expansion ratio to be the final tumescence volume divided by the initial, pre-expansion volume. The total volume of the tumescence (for a given volume injection) gives a measure of the average degree of expansion (FIG. 17C). For instance, when 20 mL were infused, the tumescent volume was 30 mL, meaning that 10 mL of tissue expanded to 30 mL, and so the average degree of expansion was 3×.

Embodiments of the invention are designed to address several core pathologies associated with chronic wounds. In illustrative embodiments, the treatment is 1) debridement, followed by 2) fast, high-volume injections of high concentration antibiotic fluid, and 3) immediate application of a skin graft. Each step is motivated by the need to return the wound healing process to an acute-like state that promotes healing. Such embodiments start with debridement to remove non-viable tissue and expose a layer of granulation tissue. This common step physically cuts or scrapes away necrotic and sloughy tissue in which pathogens thrive. A large fraction of biofilm is removed during this process as well. Afterwards a tumescent solution is infused into the viable tissue that defines the periphery of the wound bed. This step in our procedure addresses both external factors such as infection by antibiotic resistant bacteria or biofilm and intrinsic factors such as the imbalance of healing processes that prevent the chronic wound from following the normal wound-closing course. The tumescent solution is predominantly physiological saline with a high concentration of antibiotic, but does not contain a vasoconstrictor.

In embodiments of the invention, an antimicrobial agent such as cefazolin is administered at a concentration that is many times higher than the MIC of the predominant bacteria species present in the wound. The high volume antibiotic infusion forces fluid into the interstitial tissue, expanding it from the inside out. Enough volume is infused at a rate sufficient to generate an expansion of 2-5× in subcutaneous tissue thickness, where infections predominantly reside. This infusion is at a rate that is much larger than that which the body can absorb without swelling. In this context, typical "slow" rate of 1-2 mL/min is used in hypodermoclysis, where swelling is explicitly avoided (e.g. G. S. Schultz et al., *Wound Repair aRegen.*, vol. 11 Suppl 1: pp. S1-S28, 2003). The swelling (tumescence) caused by the fast, high-volume infusion should cause a volumetric expansion of 2-5× in the subcutaneous tissue. Without being bound by a specific theory or mechanism of action, we propose this expansion is the key to successful chronic wound treatment because it is the basis of 1) a dense distribution of antibiotic to infected tissue, 2) a dramatically increased hydraulic permeability (Darcy permeability) and effective macromolecule diffusion constant, 3) a flushing of the "chronic" inflammatory processes through dilution and draining of cytokines, growth factors, and other inflammation mediators that resets the wound to an acute-like state and 4) a structural and chemical disruption of biofilm.

Figure 16:
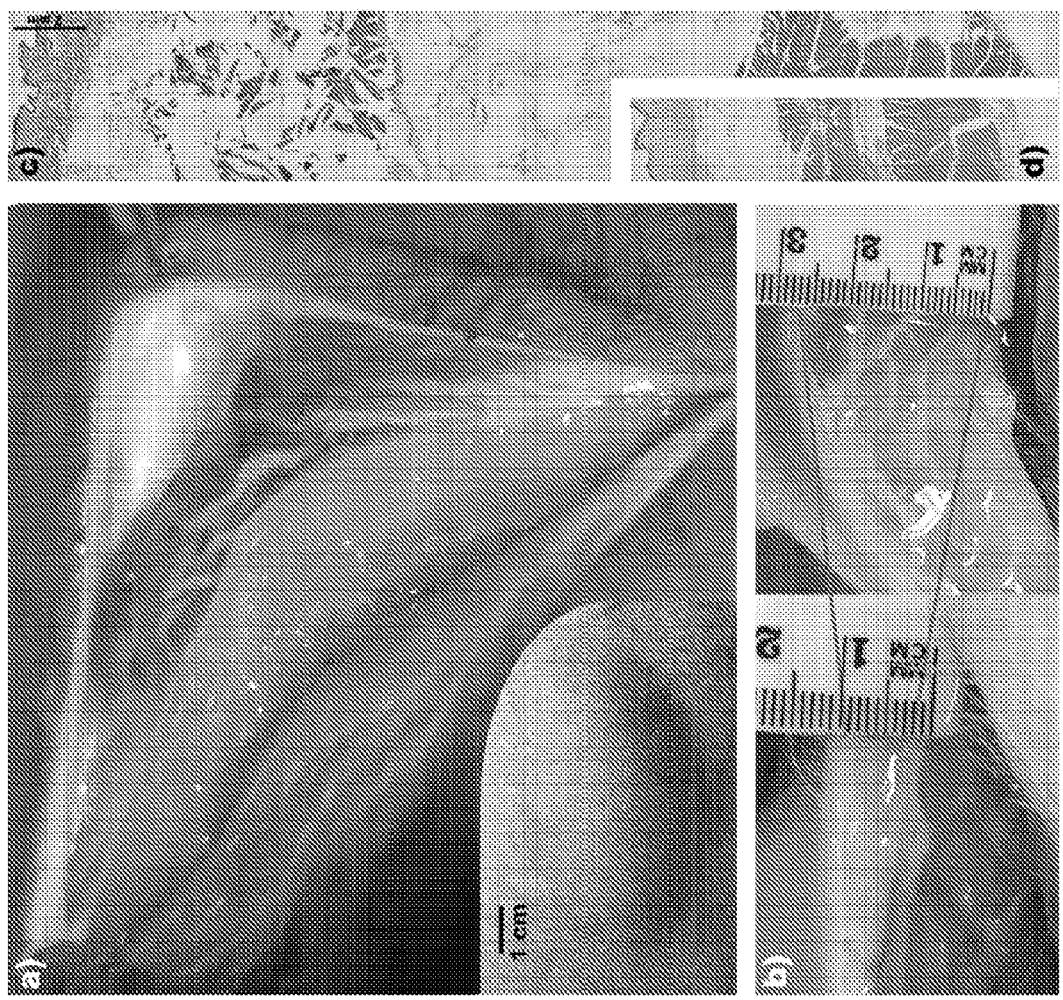
FIG. 16: Tumescent injections in subcutaneous tissue. A tumescent injection of 10 mL saline (dyed blue) causes a large, conspicuous bleb to form in the skin of a dead pig, a) inset. Slicing into it reveals that the liquid is trapped in the subcutaneous tissue, which was forced to expand to accommodate the liquid. b) Subcutaneous tissue of a Yorkshire pig swells in proportion to volume of injected saline, reaching about 4× expansion in this case. Histology of d) normal and c) tumescent subcutaneous tissue after a 5 mL saline injection, shown at the same scale.

In embodiments of the invention, an expanded tissue state that results from tumescent infusion is characterized by a dilation of the fundamental length-scale of the interstitial matrix. As the matrix expands the pores which normally hinder fluid flow and resist macromolecule/protein distribution open up. The hydraulic conductivity increases by many orders of magnitude and the apparent diffusion constant becomes equivalent to that in bulk water (see data in FIG. 17). The matrix negligibly resists flow and macromolecular diffusion is enhanced in the expanded state. The restricted circulation of chronic wounds is replaced with an almost free-flow state. Fibrin cuffs around capillaries are broken thanks to the forced expansion. The expansion/infusion process generates a dense distribution of antibiotic (see e.g. FIG. 16). The tumescent fluid is not held in a pool or bubble, but thoroughly permeates the tissue matrix, similar to in a hydrogel, and any bacteria present are surrounded by the antibiotic. An important observation here in such methods is that the interstitial matrix is capable of dilating by several times without fracture.

Figure 18:
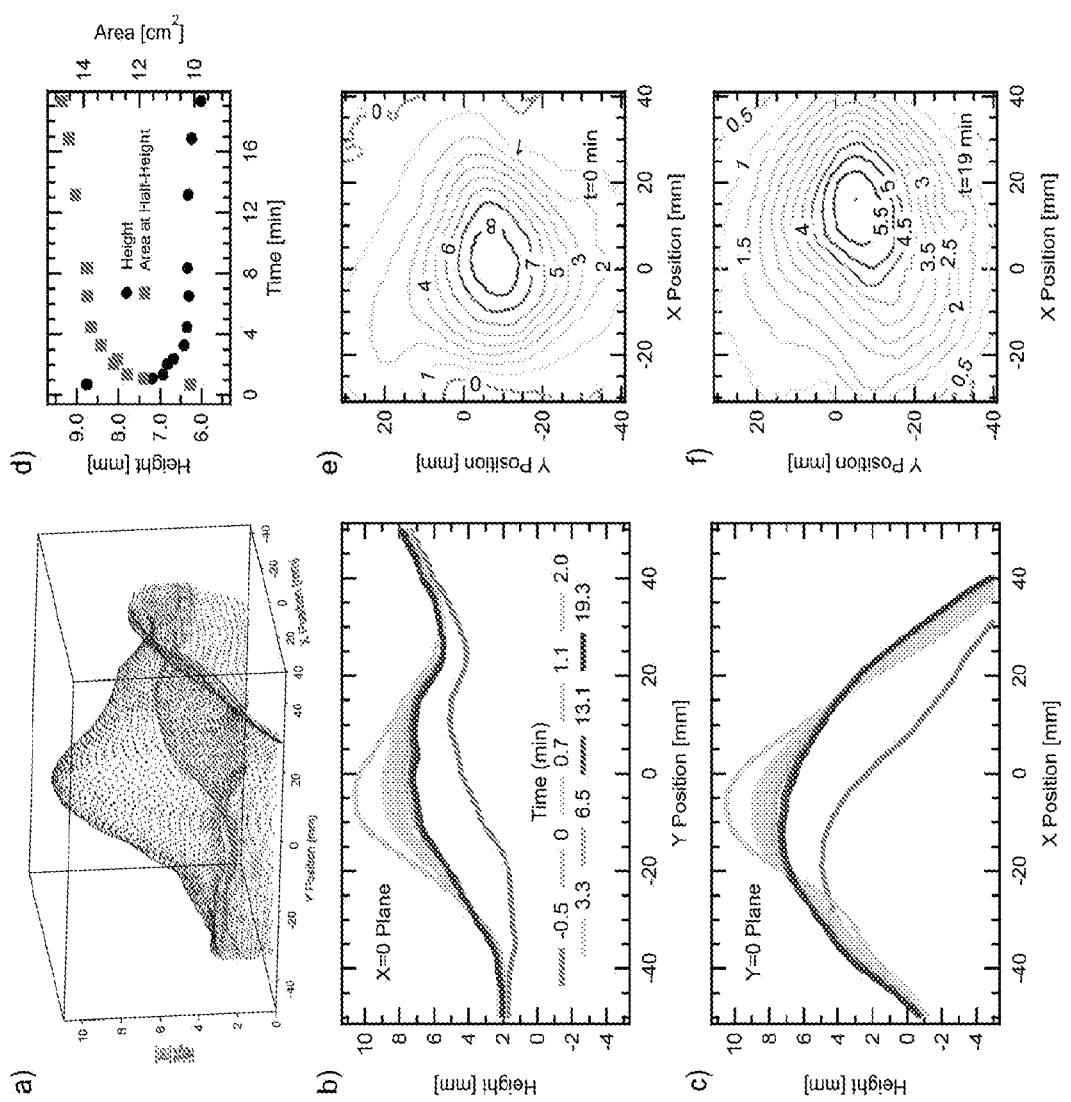
FIG. 18: 3D scans yield the tumescent skin profile over time. Panels b) and c) are lineouts of the full 3D data, shown immediately before (red) and after (black) a 20 mL injection in panel a). Two perpendicular blue lines are drawn along the tumescent surface in a) to help guide the eye. The difference between the skin surface at various times after the injection, with that before the injection, is used to calculated the tumescent height and cross-sectional area at half-height, d). Panels e) and f) are contour plots of the difference at times t=0 and t=19 min respectively.

In the expanded tissue state generated by embodiments of the invention, at least two processes compete to distribute the infusate, one acting locally, the other systemically. The first, local, method is flow in the interstitial matrix both within, and outwards from the periphery, of the tumescence. This flow remains within the interstitial tissue; the venous system and capillaries are not involved. It is a Darcy-flow type distribution where pressure differences drive fluid through a porous medium. We observe this process in both live and dead pigs. An important feature of Darcy flow in the tumescence is that the Darcy resistance depends strongly on the degree of expansion. There is nearly zero flow in unexpanded tissue, and low resistance flow in strongly expanded tissue. We define the border of the tumescence, or treatment volume as the location where the diffusion coefficient, hydraulic permeability, or Darcy resistance, return to their no-expansion value (see, e.g. FIG. 16). The Darcy flow pushes the tumescent boundaries outwards, rapidly at first, but stops after ~15 min (see, e.g. FIG. 18 that shows flow in a dead pig). This flow can optionally be accelerated by application of massage or ultrasound, but the treatment time is maximized if no mechanical stimulation is applied. The second, systemic method of fluid distribution is via the capillaries and circulation system. The infusate will be carried away from the injection region to the rest of the body via the vascular and lymphatic systems. We observe this distribution in live, but not dead, pigs. The timescales of systemic absorption vary depending on infusion volumes but are in the range of 2-3 hours for saline in healthy tissue, and the weaker circulation in chronically inflamed tissue will extend these timescales further. It is known that the use of a vasoconstrictor (epinephrine) can extend this time to >8 hrs in healthy tissue, however this also reduces the flow of health promoting nutrients/factors/cells to the wound as well. Considering the already weak circulation of the chronic wound, use of a vasoconstrictor might be suboptimal (and embodiments of the invention therefore avoid the use of vasoconstrictors).

In the tissue expansion generated by embodiments of the invention, up to 2× or 3× or 4× and up to 5× new tissue volume is created, meaning only 20-50% of matter in the expanded tissue is intrinsic and the rest came in with the infusion (with average expansion volumes being 2-5×). The intrinsic components are necessarily dilated or diluted and the local microcirculation is profoundly altered temporarily. Concentrations of cytokines, growth factors, inflammation mediators, dramatically drop, altering the working point of the countless processes that had gone awry to create the chronic wound. Further, these mediators are flushed away through the drainage (systemic absorption) of the tumescent fluid via the expanded pore network and circulation. This flushing strongly disturbs the balance of the mediators and resets the stuck, chronic healing process to a new, healing-promoting state.

Embodiments of the invention are adapted for use in conjunction with generally recommended practices such as a multistep approach to wound closure known as TIME: (T) Tissue debridement removes non-viable tissue that is an ideal environment for pathogens. (I) Infection and inflammation are minimized. (M) Moisture imbalance is corrected through the use of external dressings. (E) Epithelialization and tissue formation are promoted (see, e.g. A. Clinton et al., Lab Medicine, vol. 46, no. 4, pp. 277-282, 2015 and G. S. Schultz et al., Wound Repair aRegen., vol. 11 Suppl 1: pp. S1-S28, 2003). Our approach addresses each of these steps synergistically. Debridement is performed as usual to expose viable tissue and create acute-like conditions on the surface of the wound. Infection is addressed through the volumetric permeation of the tissue with high concentration antibiotic that also disrupts quorum sensing and structure critical for biofilms. The chronically inflamed state is given a serious push out of its working point by the saline flush that resets the imbalance of inflammation mediators. Moisture is provided from the inside out by the saline itself. The saline continues to seep out of the wound bed hours after the procedure, preventing desiccation and the reinfection of the surface. Immediate skin grafting (contrary to recommended practice of first ensuring the absence of infection) provides almost immediate epithelialization of the wound bed to close it.

In illustrative embodiments of the invention, a large volume (from about 100 mL to 2 L, depending on the size and extent of the wound) of tumescent solution is prepared by adding an antibiotic at a concentration shown to be effective at treating the relevant bacteria present in the wound to physiological saline, or other isotonic fluid. For example, a concentration of 1 g/100 mL cefazolin, as Dr. Barry Silberg uses in DAD [51, 52], is above the MIC for most, if not all, MRSA strains [61], and is safe to infuse into tissue. In fact, another cephalosporin, Ceftriaxone, has been shown to be save at 35 times higher concentrations [22]. In some embodiments, other additives may be added to the solution including but not limited to epinephrine, sodium bicarbonate, and lidocaine may be added to the solution to impart additional properties such as vasoconstriction, vasodilation, pain-relief, slower diffusion, or others. The patient is optionally placed under general or local anesthesia to help with pain and/or comfort. The wound is debrided before tumescent antibiotic administration begins usually with sharps until normal, well-vascularized tissue appears [2]. The usual sterility procedures are followed.

Tumescent antibiotic delivery is typically administered as with to tumescent anesthesia, which has been described extensively elsewhere [37, 42]. Briefly, a small incision is made in the skin or on the wound bed directly. A cannula or microcannula is inserted through the incision and directed through subcutaneous tissue underneath, or slightly to the side of the wound, along a linear path. As the cannula is slowly retracted, again along a line, the tumescent solution is injected into the tissue, causing it to swell (tumesce). Once the cannula has been retracted back to the incision site, it is reinserted along a different line that makes a small angle with the first line, and the solution is injected as with the first line. This procedure is repeated with a plurality of infusions in a fan-like pattern with the goal of tumescing the entire region underneath and circumscribing the wound. Additional incisions may be made around or on the wound to facilitate injecting from different directions and tumescing the entire wound bed. The method of tumescent injection can be done by different means to achieve similar ends.

The tumescent injection infuses antibiotic solution throughout the subcutaneous tissue. Supporting evidence is given in the EXAMPLES section below, but here we present the conclusions. Subcutaneous tissue expands in response to the pressure of the injection, expanding up to a few times its original thickness, and trapping the antibiotic solution within it in a gel-like state. Antibiotics fully permeate the tumesced tissue, reaching even the smallest pores. This fact can be deduced from the observation of the tumescence, which is remarkably smooth and uniform. As the tumesced tissue has expanded ~2×, any ~1 $mm^3$ size volume of unexpanded tissue within it would appear on the surface as an obvious "hole" or divot, which is not observed. If smaller sized volumes ~1 $\mu m^3$ remain unexpanded within the tumescence, the injection either overtakes them as it spreads over the 1-10 min timescale, or the antibiotic spreads to them aided by the high-diffusion constant (equivalent to the self-diffusion of water) in the tumesced state.

Achieving sufficient tumescence is important for keeping the high concentration of antibiotics localized long enough for the antibiotics to be effective. It was not known by people experienced in the art that one can increase the residence lifetime of antibiotics in tissue as can be done by the methods disclosed herein. Tissue expansion helps in two ways: 1) a store or depot of antibiotic-rich fluid is contained in the immediate vicinity of every bit of tissue, and 2) the density of lymph vessels and capillaries that drain away the tumescent fluid is reduced. In other words, greater expansion implies more infused liquid, and the reduced ability of the body to remove the excess volume. The rate of spreading through permeation into surrounding, unexpanded subcutaneous tissue is proportional to the perimeter of the tumescence (flow through the skin above or fascia below is negligible), so smaller perimeter to volume ratios favor longer containment.

Skin grafting may follow after antibiotic infusion has been completed. Grafting is almost never done on infected wounds until the infection has been cleared because it does not take. In this case grafting may be done immediately which eliminates the necessity of an additional surgical procedure. Post-operative instructions and care for the patient should favor keeping the infusate localized. For example, minimizing the motion of the extremity (if in an arm or leg) keeps the draining lymph flow down. Physical/mechanical manipulation of the wound should be avoided at least early on.

Chronic infections, and in particular, antibiotic resistant ones, can be safely and effectively treated using embodiments of the invention disclosed herein. Local concentrations are above MIC, yet systemic doses remain safe. It was not appreciated until now that tumescent injection can be used to treat chronic infections, including antibiotic-resistant ones, for various reasons, some of which we have shown to be false and/or misleading. 1) Swelling and edema in HDC are considered adverse effects to be avoided. We use the tumescence to saturate and disperse antibiotic within the tissue, yet the tissue recovers unharmed. Tumescent anesthesia regularly achieves extreme subcutaneous swelling yet there remain zero reports of swelling-related adverse effects. 2) Subeschar antibiotic clysis attempts to achieve high antibiotic concentration directly in the infection site, but that technique is also non-tumescent. Infusions are ~1 mL/10 cm$^2$ [31], or slow drips from IV [29]. Low-rate and/or low-volume infusions may remain contained in rivulets or localized pools, which do not fully and uniformly saturate the tissue with antibiotics. Distending the tissue to both saturate it thoroughly and keep the antibiotic localized for an extended amount of time are key to our invention. In fact, some of the subeschar antibiotic clysis literature concludes that infusion directly into the wound is no different that infusion away from the wound [32]. 3) Observations of blebs or "camel-hump" subcutaneous injections are externally observed to soften and spread quickly. Intuition says that once the swelling dissipates, the tumescent fluid is also gone and antibiotics infused in that manner would not be localized sufficiently long for them to have any affect. On the contrary, we have demonstrated that despite the softening and spreading of the tumescence, the fluid remains localized for many hours. 4) The pharmacokinetics of subcutaneously delivered antibiotics—when done in small volumes—show that the peak serum level occurs 1-3 hours post injection. In fact, the goal is usually to shorten the time to peak serum, because that is associated with a higher peak serum concentration, and greater drug efficacy, and so agents such as hyaluronidase are sometimes used in embodiments of the invention. Since the time to peak serum is closely tied to the time the injected fluid remains in the tissue, objections have been raised saying that subcutaneously delivered antibiotics do not remain at the injection site long enough for the antibiotics to act locally. Our observation that the tumescent fluid can remain localized for a time that is long compared to the half-life of many bacteria sidesteps this pharmacokinetic objection. Further, Klein's data on the serum levels of large volume tumescently delivered antibiotics for prophylaxis [26] do show that the time to peak serum level can be extended out to many hours with a tumescent injection and that the tissue concentration remains high during this time.

As noted above, in typical embodiments of the invention, the volume of injection (tissue expansion) is chosen to affect residence time in tissue. The tumescence region is measured in space and time to achieve stated goals; such as by i) 3D imaging; ii) CT; iii) magnetic resonance imaging; iv) indentation or other stress-strain method; v) palpation; vi) ultrasound; vii) backpressure on injection regulator. Dispersal is mostly achieved by the injection and tumescent dynamics directly. In all cases, ultrasound is not used. Antibiotics are chosen via an MIC table or time-dependent MIC table. Skin grafting is performed subsequent to tumescent infusion, during the same procedure. Post-operative care is chosen to extend tissue residence time of infusate. Optionally, hyaluronidase or other edema-reducing agent is added to the solution in some embodiments of the invention. Drugs such as epinephrine, which affect residence time in tissue, may be employed (or alternatively may be avoided) in embodiments of the invention. Drugs that are modified to stay in tissue longer are used. The drug concentration is chosen so that local level of antibiotic is so large that a bacteriostatic drug becomes bactericidal. While human patients are the focus of this methodology, in certain instances, this method is performed on an animal such as a dog or cat or horse. Additional injections or infusions are performed periodically or continuously (via IV for example) to maintain tumescence in the affected regions for extended periods of time.

Further aspects and embodiments of the invention are disclosed in the following examples.

Examples

Experimental Background

Figure 2:
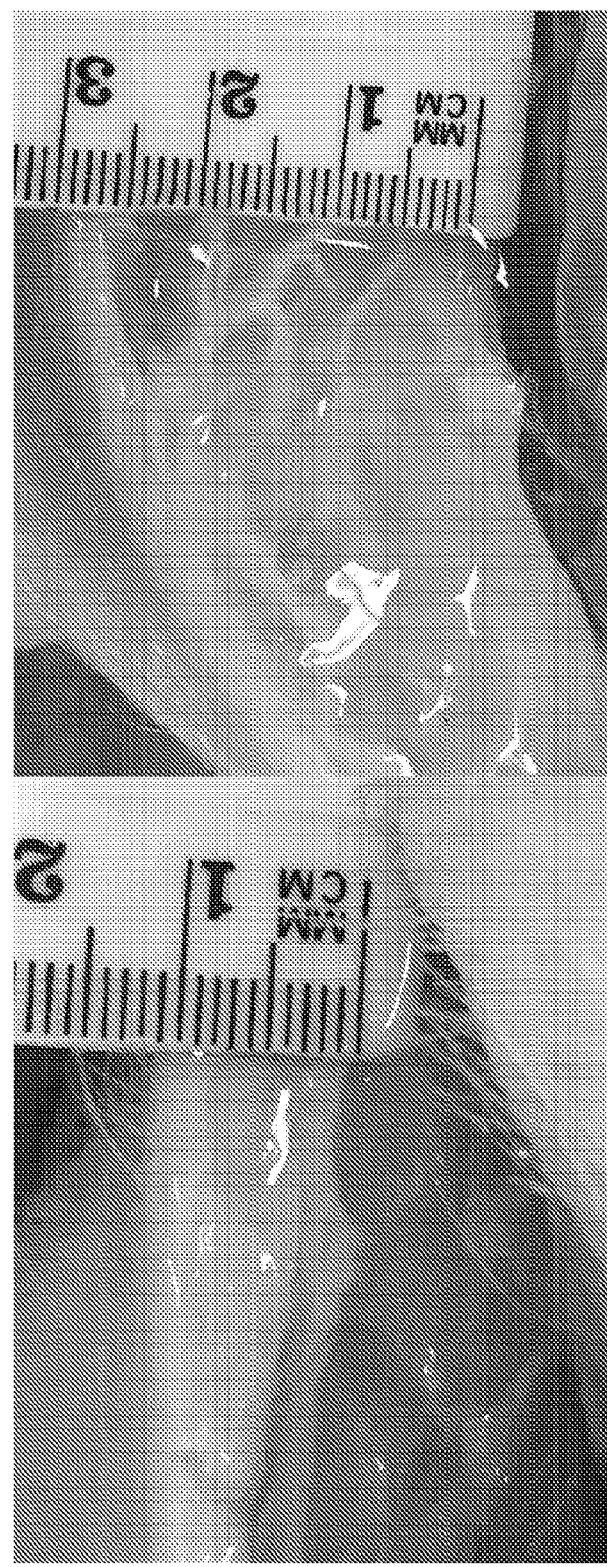
FIG. 2: Expansion of the subcutaneous tissue of a dead, adult Yorkshire pig upon injection of saline (without dye). In this example, the tissue expands from about 8 mm to 25 mm. The degree of expansion is controlled by the amount of fluid injected.
Figure 3:
FIG. 3: A tumescent injection of green-dyed saline is performed in the thigh of a healthy, deceased, juvenile Yucatan pig. Afterwards, an incision is made completely through the tumescence, and the skin is cut away to reveal the extent, thickness, and permeation of the injected saline. The saline injection forced the expansion of subcutaneous tissue to accommodate its volume, trapping the injected fluid within the expanded extracellular matrix.

FIG. 1 is a picture of tumescence in healthy subcutaneous tissue of a recently deceased juvenile Yucatan pig. Saline with blue dye was injected subcutaneously, causing conspicuous swelling of the skin above. Slicing into the swollen tissue and opening the incision reveals that the injected fluid is trapped in the subcutaneous tissue matrix, between the fascia and dermis. The extracellular matrix of the subcutaneous tissue expands to accommodate the liquid, forming a jelly-like substance that holds together. Notice in FIG. 1 that very little, if any, blue-dyed saline runs down from the swollen tissue. It is mostly held in place. A similar experiment in a healthy, recently deceased adult Yorkshire pig (with saline not containing dye) is shown in FIG. 2. On the left, a cross section of subcutaneous tissue is shown in a region without a tumescent injection. The right shows a cross section of tumesced subcutaneous tissue nearby where the control cut was made. Measurements reveal that the subcutaneous tissue has expanded by over 3× in this example, and up to 10× in experiments not shown. The extra volume overtaken by the tissue is comprised of the tumescent solution, which has thoroughly permeated the tissue to the point of uniformly increasing its volume by several times. FIG. 3 shows a third example of a tumescent injection of green-dyed saline in the hind leg of a healthy, adolescent minipig. A cut was made through the tumescence to reveal the muscle underneath, and the skin was removed to reveal the extent and uniformity of tumescent fluid permeation in the subcutaneous tissue.

While the examples shown are in the healthy subcutaneous tissue of ex-vivo (recently deceased) pigs—which are known to have similar skin as humans [60]—we expect the healthy tissue beneath and surrounding chronic wounds in humans to have similar properties. The tumescence will also overtake the inflamed and/or infected tissue of the wound, although perhaps somewhat differently, delivering a high concentration of antibiotics directly to the impacted tissue.

Figure 4:
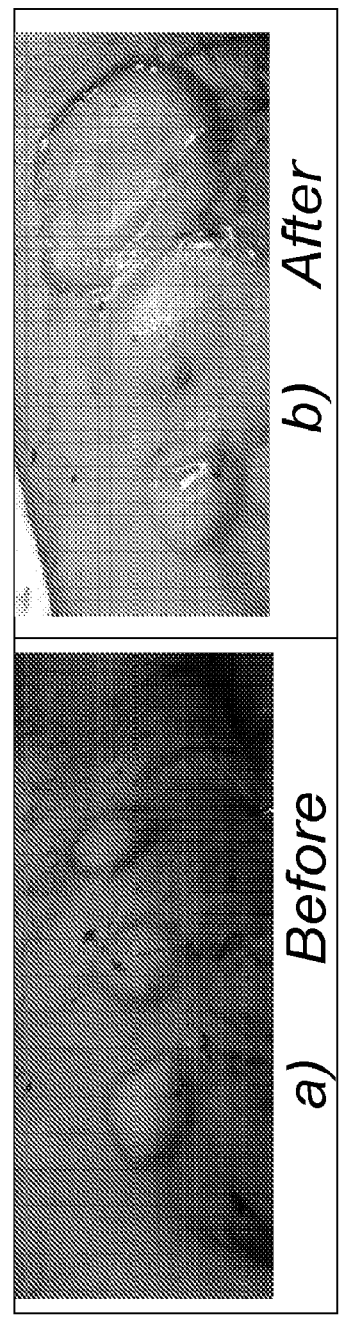
FIG. 4: Three equal-volume tumescent injections before (a) and after (b) the passage of time (left spot), massage (middle spot), or application of ultrasound (right spot). Massage and ultrasound were performed for 2 minutes each with similar ultrasound heads applying the same pressure with the same motion pattern. The ultrasound intensity was 3 W/cm$^2$.

The dynamics of the tumescence are initially rapid but slow down considerably. Upon bolus injection, the tumescence has well defined edges that soften and smooth out over the course of a minute. Over longer times, it spreads in area and is eventually completely absorbed by the body, leaving little, if any, evidence of its existence. Massage accelerates the spreading process. FIG. 4 displays two photographs of three tumescent injections in a deceased juvenile Yucatan pig before and after 1) the passage of time ("control", left spot), 2) massage ("massaged", middle spot), and 3) application of ultrasound ("sonicated", right spot). The edges of the control are visibly softer (not as clearly defined), but there is little spreading in area. Both the massaged and sonicated spots have spread considerably in area compared to the control but there is little qualitative difference between the massaged and sonicated spots.

Figure 5:
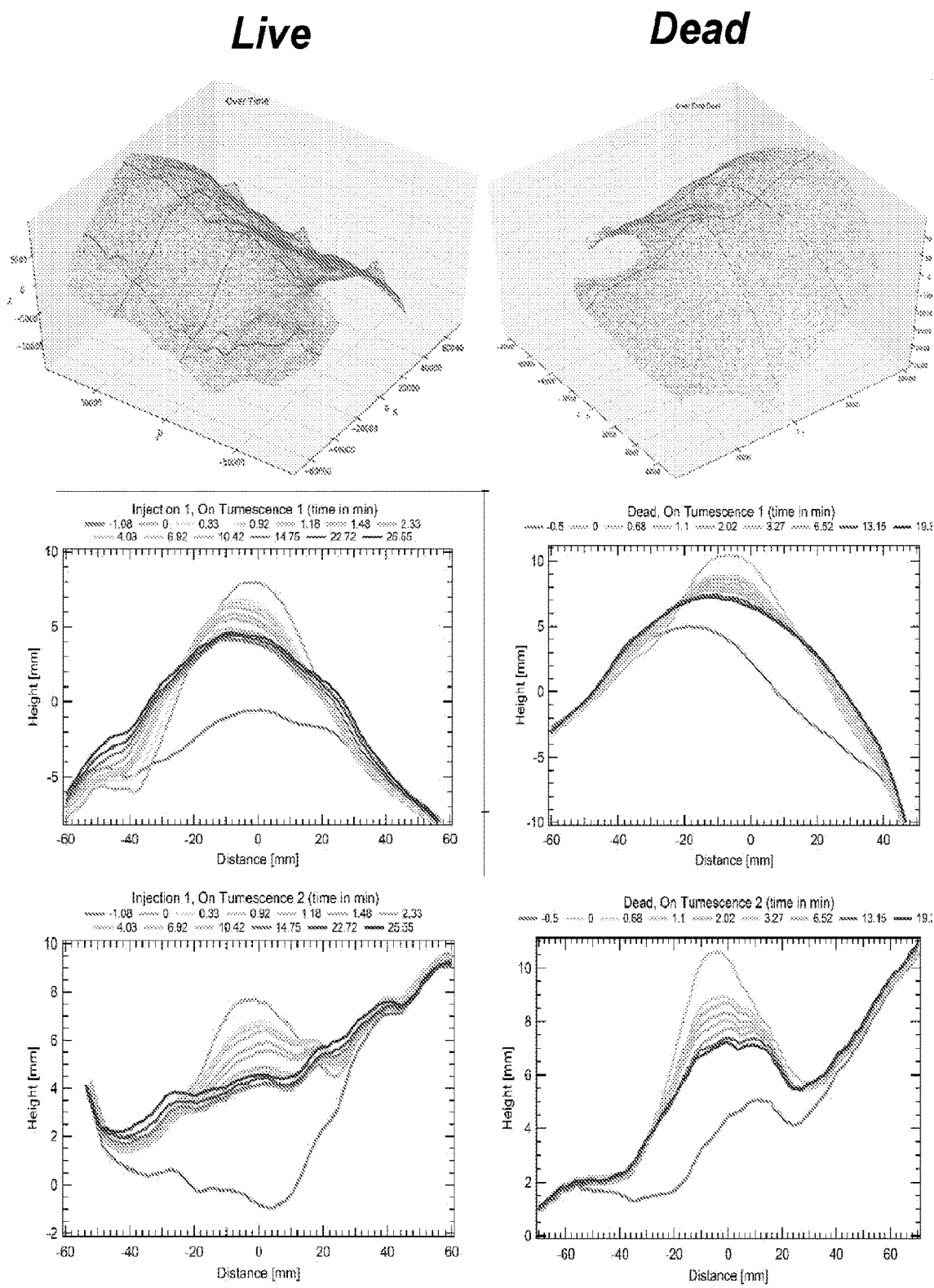
FIG. 5: The evolution of 20 mL injections into the subcutaneous tissue of a live and dead juvenile Yucatan pig. The dynamics of the tumescent injection are observed for about 25 min. Lineouts on the tumescence are displayed along perpendicular directions to characterize the spreading of the tumescence in 2D. Lineouts off the tumescence are not displayed but were taken to verify the alignment of individual scans.

The tumescence shape before and after massage and/or sonication can be more precisely characterized with the use of 3D scanning. 3D scanners extract information on the 3-dimensional structure of the skin surface and are useful to better appreciate the initially rapid dynamics of a tumescent injection over time. We scanned a 20 mL tumescent injection in the healthy subcutaneous tissue of an anesthetized, live pig periodically over 25 min. Lineouts of the skin profile are shown in the left-hand column of FIG. 5; the top row is a point cloud reproduction of the pig's skin surface, while the middle and bottom rows show lineouts across the tumescence in perpendicular directions to characterize the spreading in 2D. The tumescence changes shape very rapidly early on, dropping more in the first two minutes than in the subsequent 20. As the tumescence peak drops, the width increases. We repeated the experiment in a recently deceased pig, shown in the right-hand column of FIG. 5. As circulation has ceased in the dead pig, the usual pressure differences (Starling forces) that lead to perfusion are suppressed. The qualitatively similar evolution of the tumescence in a live and dead pig indicates that the localized, tumescence pressure is the main driver of the spreading early on, not the usual perfusion, which has undoubtedly been seriously altered by the tumescence.

Figure 6:
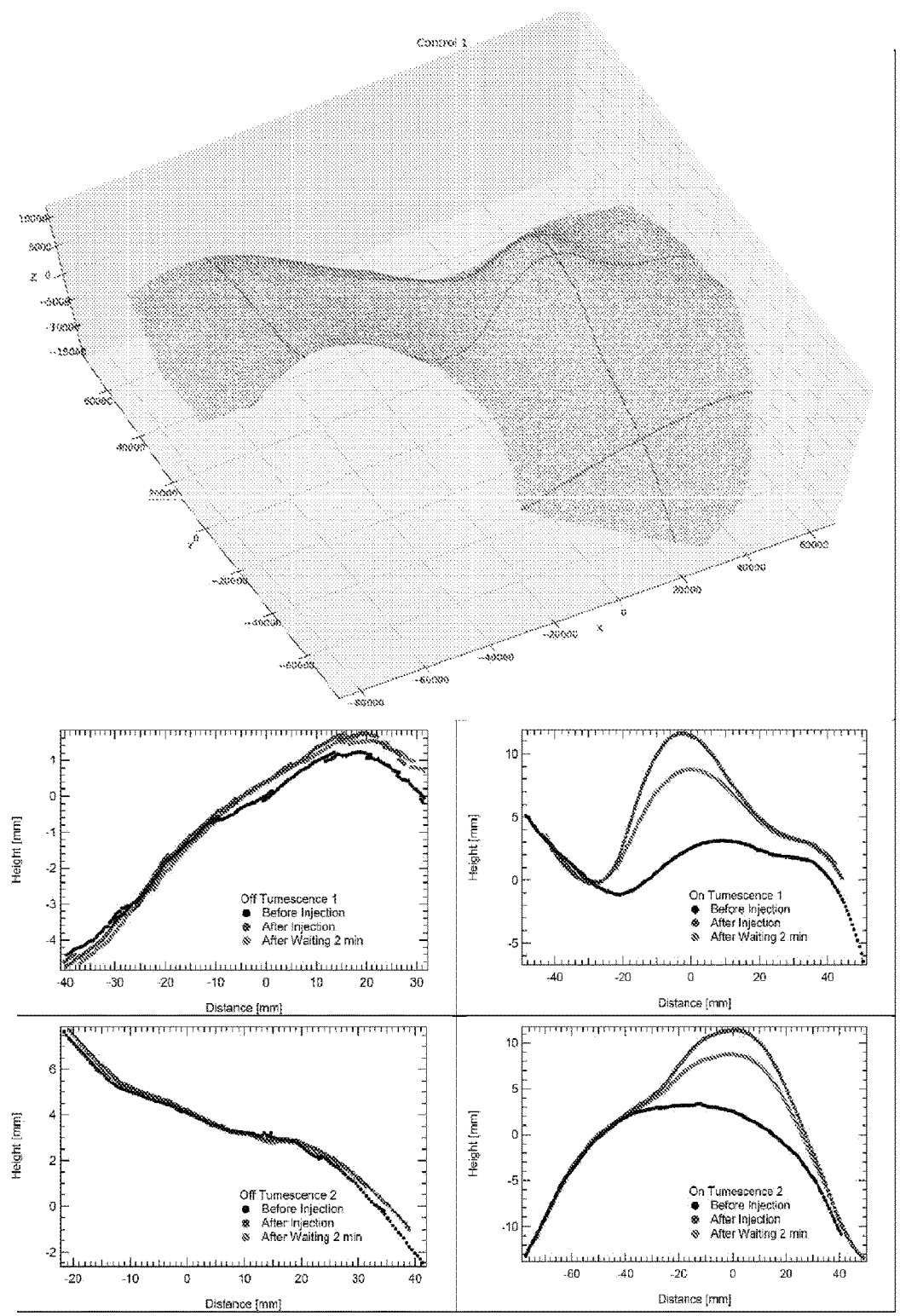
FIG. 6: Spreading of tumescent injection on its own. No massage is applied. The location of injection is symmetrically opposite to the location of the massaged injection in FIG. 7. Lineouts off the tumescence are shown in order to verify the scan alignment.
Figure 7:
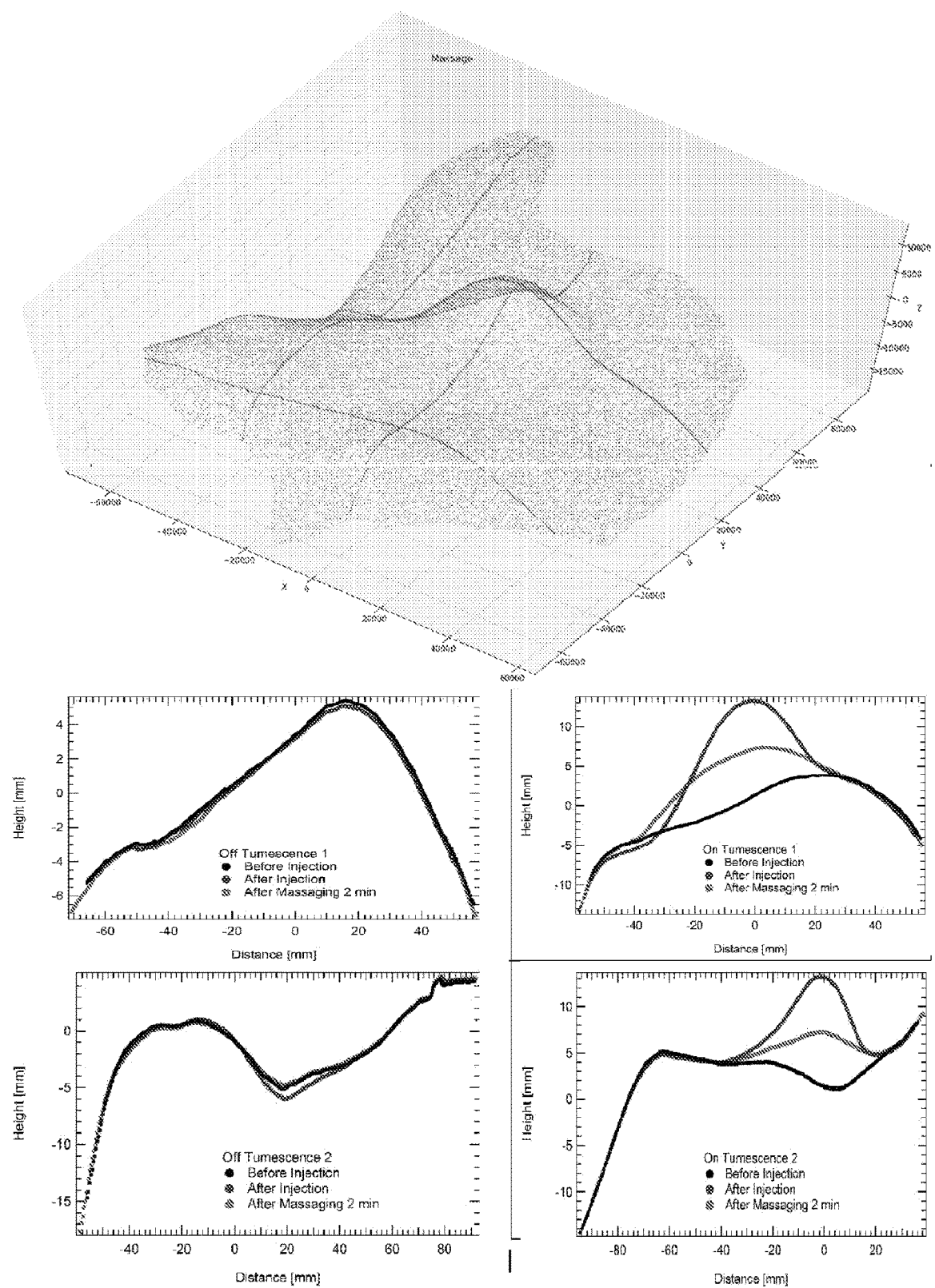
FIG. 7: Spreading of tumescent injection with massage. The location of injection is symmetrically opposite to the control injection location in FIG. 6, and massage is performed for 2 minutes. Lineouts off the tumescence are shown in order to verify the scan alignment.

We further studied whether massage helps disperse tumescence in a healthy young Yucatan pig by taking a 3D scan before and after massaging. A 3D scan was taken before the tumescent injection (t=0), followed by a 10 mL tumescent injection at t=30 sec. The injection was done smoothly over 10 seconds. Another 3D scan was taken at t=50 sec to characterize the tumescence shape before the test. The test (waiting or massaging) was administered for 2 minutes starting at t=1 min. For the control experiments, we simply waited for the 2 minutes duration. The control injection was done on the symmetrically opposite side of the pig to minimize variation in the tissue. Finally, a scan was done after the test at t=3.5 min to assess the degree of spreading. The massaged spot and its control are shown in FIG. 7 and FIG. 6 respectively. The tumescence softens and spreads considerably on its own, but massage does accelerate the spreading compared to the control. The alignment of the scans can be verified by looking at the lineouts away from the tumescence, which should overlap. Lineouts across the tumescence display the extent of swelling in perpendicular directions.

Figure 8:
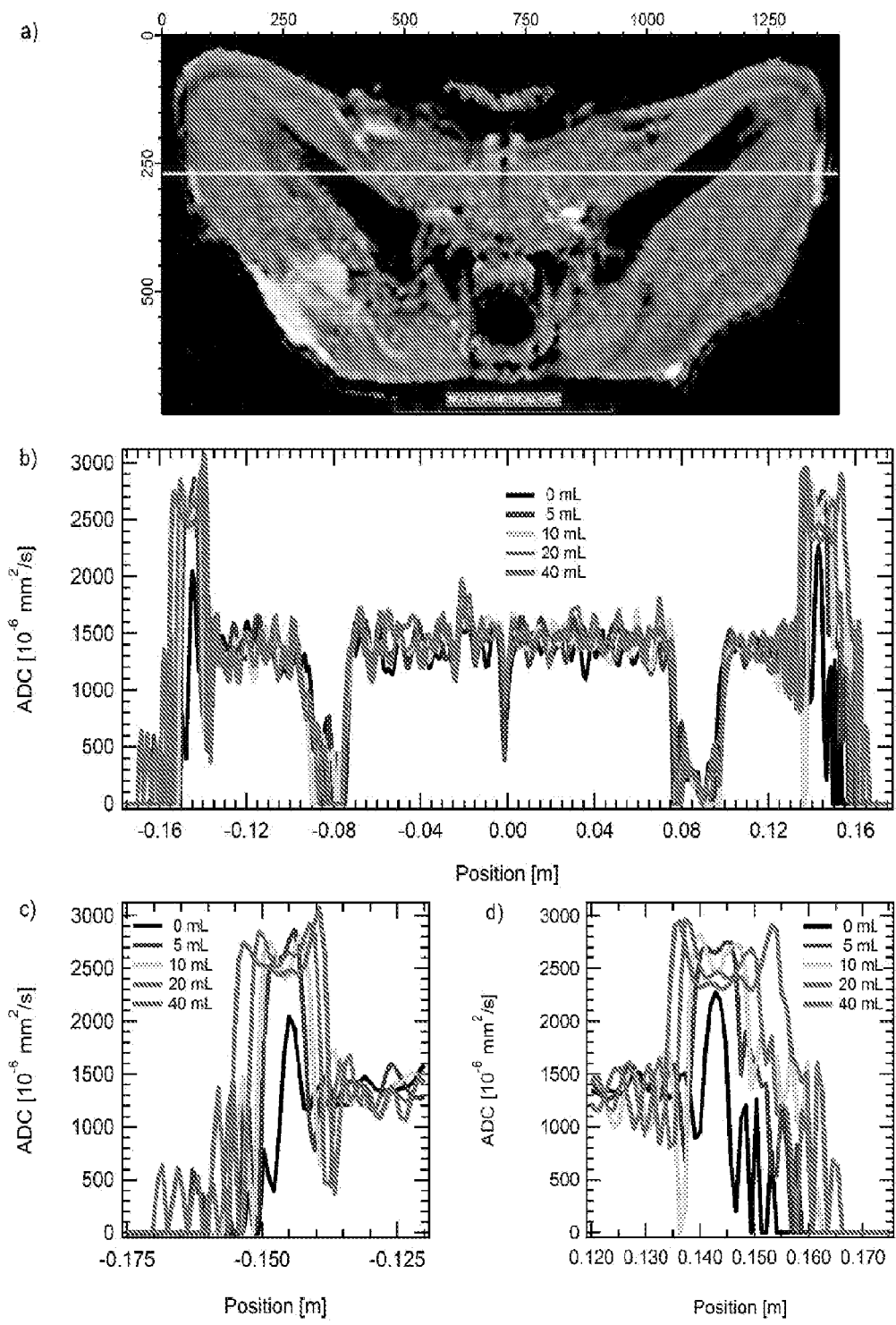
FIG. 8: Diffusion-Weighted MRI imaging of tumescence. Image a) is an axial cross-section of the apparent diffusion coefficient (ADC) in a Yucatan pig before tumescent injections are performed. This particular cross-section is taken between the pig's hip and knees while it is lying on its back; the black internal regions are femurs and vertebra. Dark regions represent low values of the ADC, whereas lite shades represent higher values of the ADC. Lineouts of the ADC taken along the green line in a) are shown in b), c), and d) for images taken with different volume tumescent injections performed subcutaneously in the same locations on the outer part of the thighs. Inspection of b) affirms that the images are aligned properly, as the dips at the locations of the femurs (at +−0.075 m) are all in the same position. Panels c) and d) are zoomed into the regions of tumescent injection in the pig's right and left leg respectively.
Figure 9:
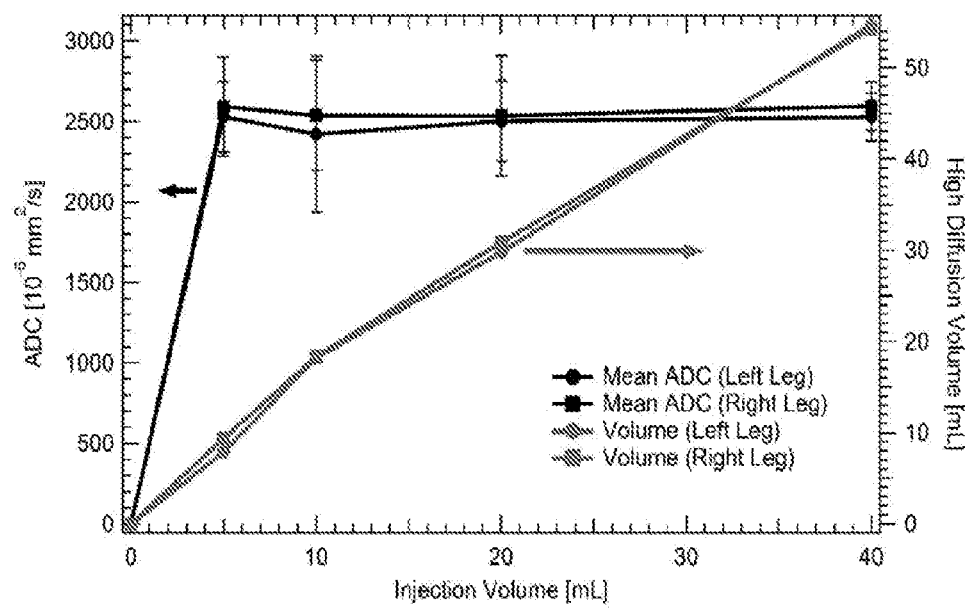
FIG. 9: The apparent diffusion coefficient of subcutaneous tissue rises to a value of $2500 \cdot 10^6$ mm$^2$/s after tumescence with 5 mL saline, and remains at that value as more volume is injected, although the total tumescent volume grows roughly linearly with injection volume.

The volume of saline injected determines the extent (both in area and thickness) of tissue expansion. To study the extent of expansion as a function of injection volume, we performed diffusion-weighted magnetic resonance imaging (DW-MRI) [62]. This type of imaging measures the "apparent diffusion constant" (ADC) of tissue, which is very small in normal subcutaneous tissue and can grow by many orders of magnitude in edematous [19] or tumescent tissue. Tumescent saline injections were performed in the subcutaneous tissue of the hind limbs of an anesthetized Yucatan pig, and the extent of tumescence was quantified with DW-MRI. Diffusion images were acquired before any injection (0 mL) (FIG. 8a), and after injections of 5 mL, 10 mL, 20 mL and 40 mL total in the same location of each leg (without moving the cannula/needle). As more liquid is injected, the tumescence grows both in area and thickness. Lineouts of the ADC through the tumescent regions (FIG. 8b-d) indicate that the tumescence spreads both inwards and outwards, roughly centered on the initial location of the subcutaneous tissue. The ADC is seen to rise to a value of about $2500 \cdot 10^{-6}$ mm$^2$/s—equal to the self-diffusion coefficient of water [63]—after injections of volumes as low as 5 mL, and remains at that level as more liquid is injected (FIG. 9). In other words, injections as small as 5 mL are sufficient to expand the extracellular matrix enough so that the matrix itself does not noticeably inhibit the diffusion of water. Water may diffuse freely on the molecular level, but it is still held in place at the macroscale (does not run in FIG. 1, FIG. 2, or FIG. 3).

Figure 10:
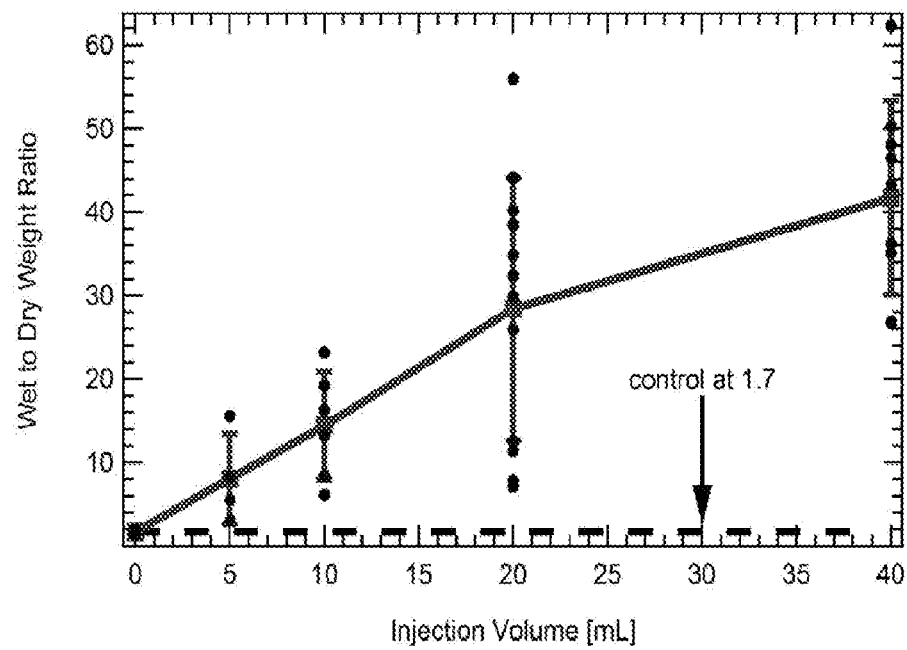
FIG. 10: The expansion of subcutaneous tissue upon tumescence is quantified by removing many small (about 0.5 g) samples of tumesced tissue from the 10-100 times larger tumescence. Samples are weighed before and after desiccation to quantify the amount of water content, and the ratio is plotted. The scatter amongst injections of the same volume is due to variations of the tissue within the same tumesced volume; blue points are averages and error bars indicate the standard deviation. Control samples—measured without a tumescent injection—have a wet to dry weight ratio of 1.7.

Although the ADC saturates very quickly, as more liquid is infused 1) the already-expanded tissue continues to dilate while 2) the infusion overtakes fresh, unexpanded tissue. We removed many small samples (about 0.5 g) of tumescent tissue from the much larger tumescence (about 10× larger for 5 mL injections, and 100× larger for 40 mL injections), and weighed them before and after desiccation. The results, shown in FIG. 10, indicate that the tissue expands proportional to the volume injected for volumes in the range tested (up to 40 mL in one spot). Control samples (taken from regions without injection) have a wet-to-dry-weight ratio of 1.7 while tissue tumesced with 20 mL saline has a ratio of about 27 on average—a ratio of about 16. Variation of the wet-to-dry-weight ratio of samples is due to variation of the tissue within the same tumescence volume itself—not variation from injection to injection. For example, as seen in FIG. 1, although the tumesced tissue looks blue from the dyed saline, there are white streaks visible in it that contain a lower saline fraction, and, of course, the edges of the tumescence must transition smoothly to the normal tissue state. While taking samples, we attempted to avoid regions with visible white streaks (fatty tissue) and focused instead on the more transparent, more-water-filled spots (see FIG. 1). The white areas are expanded as well, but to a lesser degree. Obviously for the smaller volume injections, it was impossible to avoid the streaks embedded within the tumescence and more found their way into the samples. Consequently, the points on the graph should be interpreted as representative of local maxima in expansion/tumescence, not random samples. The average degree of expansion can be extracted from the DW-MRI data in FIG. 9, where it is seen, for example, that a 20 mL injection leads to 30 mL volume of high diffusion. In other words, 10 mL of subcutaneous tissue expanded to 30 mL, an expansion of 3×.

Figure 11:
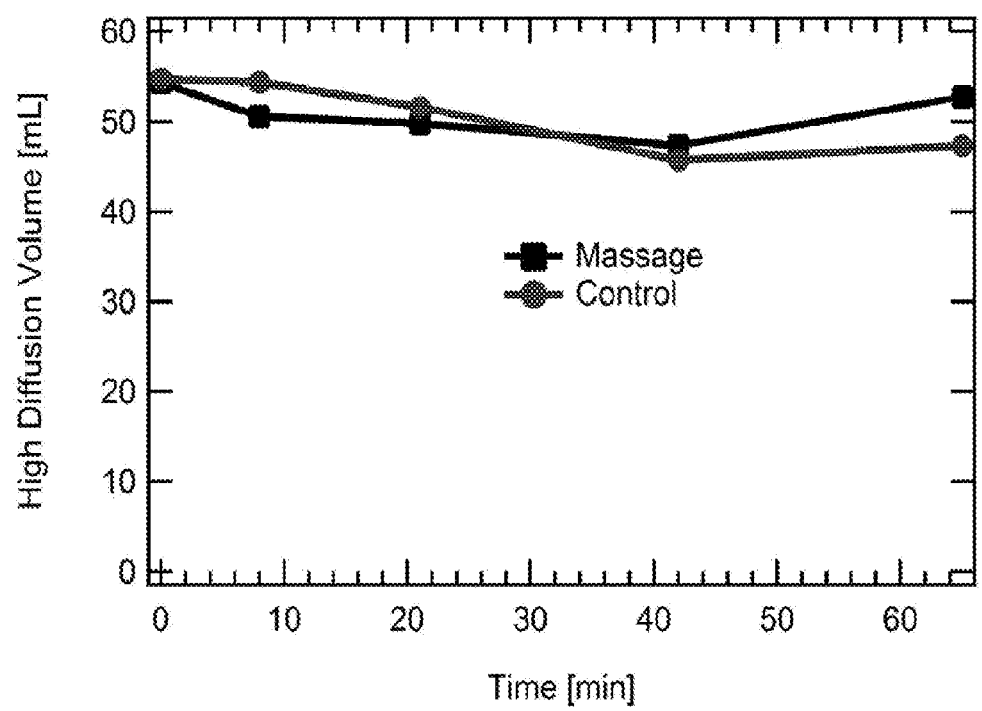
FIG. 11: Volume of tumescence (high ADC volume as measured by DW-MRI) induced by a 40 mL injection. While the shape of the tumescence is seen to change, the total volume stays roughly constant within experimental uncertainty over the 65 min of the experiment.

Looking carefully at the evolution of tumescence as seen in DW-MRI images, we find that as the tumescent area expands, the total tumescent volume is roughly constant (FIG. 11) for both massaged and control spots for at least an hour. This complements our observations from 3D scans, which show spreading through the skin surface, and do not show the full 3D tumescent volume. Apparently, the time scale for localized spreading—determined by Darcy-law flow through non-homogeneously expanded interstitial tissue driven by tumescent and elastic pressure—is short. This occurs on a time scale of <5 min. This can be compared to the time scale of tumescent fluid absorption and spread to the rest of the body, which is longer than 1 hour.

To more accurately determine the timescale over which the local antibiotic concentration remains high, we performed CT scans over a long time period. Tumescent injections of 20 mL, 10 mL, 5 mL, and 2.5 mL (2 each) saline containing 2 g/100 mL iodine contrast were performed in subcutaneous abdominal tissue of a healthy adult Yucatan pig as single bolus doses that were completed in <20 sec. The distribution of iodine was observed with CT over the course of seven hours. While in principle the contrast might have different absorption kinetics than diluted antibiotics, we don't expect the interstitial fluid dynamics to be much different as the fluid viscosity is similar and the molecular size of antibiotics and the iodine contrast are comparable.

Figure 12:
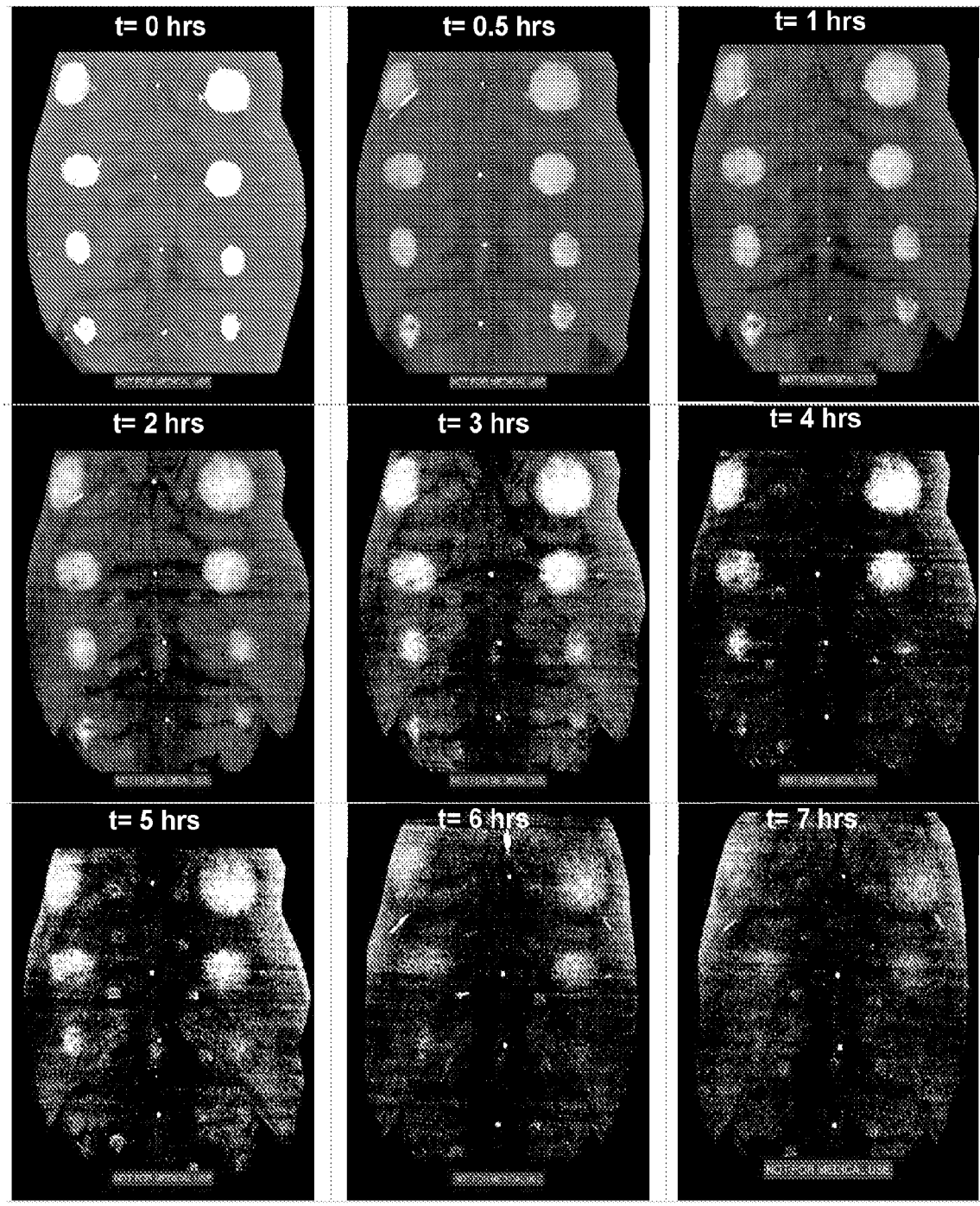
FIG. 12: CT images showing the time evolution of various volume injections of saline with contrast agent into the subcutaneous tissue of an adult Yucatan pig. Images are taken at time t=0, 30 min, 1 hr, 2 hrs, 3 hrs, 4 hrs, 5 hrs, 6 hrs, and 7 hrs. Two injections of 20 mL, 10 mL, 5 mL, and 2.5 mL each were done on opposite sides of the pig's abdomen, with large volume injections closer to the pig's head (top of images) and smaller ones towards the feet (bottom of images). The white dots along the center of the abdomen are markers placed in the same axial plane as the injection location. Image contrast and gamma values have been changed for each image for ease of viewing. The value recorded in the photo is the maximum attenuation in a lineout perpendicular to the surface (Maximum Intensity Projection [MIP] mode).

FIG. 12 displays the evolution of the tumescence over 7 hours. The figures are CTs viewing the abdomen of the pig with the head towards the top of the figure. Tumescent injections are seen as 4 rows, and 2 columns of large circular white regions, with injection volumes 20 mL, 10 mL, 5 mL and 2.5 mL from top row to bottom. There is one column of 4 tiny white dots along the center of the abdomen that are skin markers placed in the same axial plane as the location of the injections for reference. It is clear that the iodine concentration may remain high for several hours. While the 20 mL injections are clearly visible for 5 hours, the 2.5 mL injections are easily seen for only 3 hours.

Figure 13:
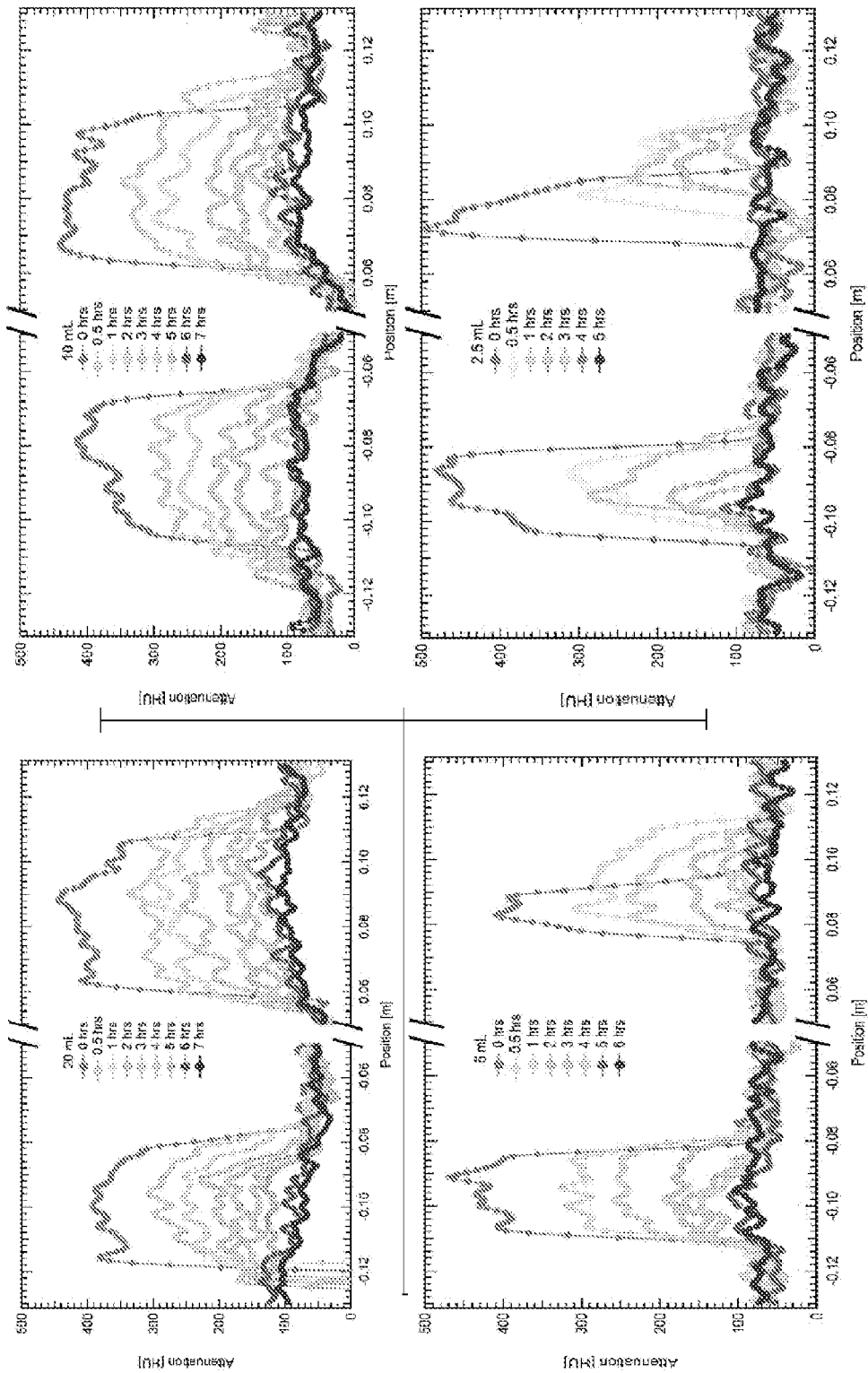
FIG. 13: Lineouts of CT images shown in FIG. 12 (parallel to image plane). Each point displayed is the maximum attenuation in a lineout perpendicular to the surface (Maximum Intensity Projection [MIP] mode).

Lineouts of the CT images taken parallel to the skin surface are shown in FIG. 13. Each value along the lineout represents the max attenuation value below that point on a line perpendicular to the surface (Maximum Intensity Projection mode). For comparison, we measured the attenuation of a vial of pure infusate to be 500 HU, and the attenuation of normal subcutaneous tissue to be about −90 HU. A concentration equal to at least half the initial value (or attenuation of 155—half way between the extremes) is maintained for at least 4 hours.

Figure 14:
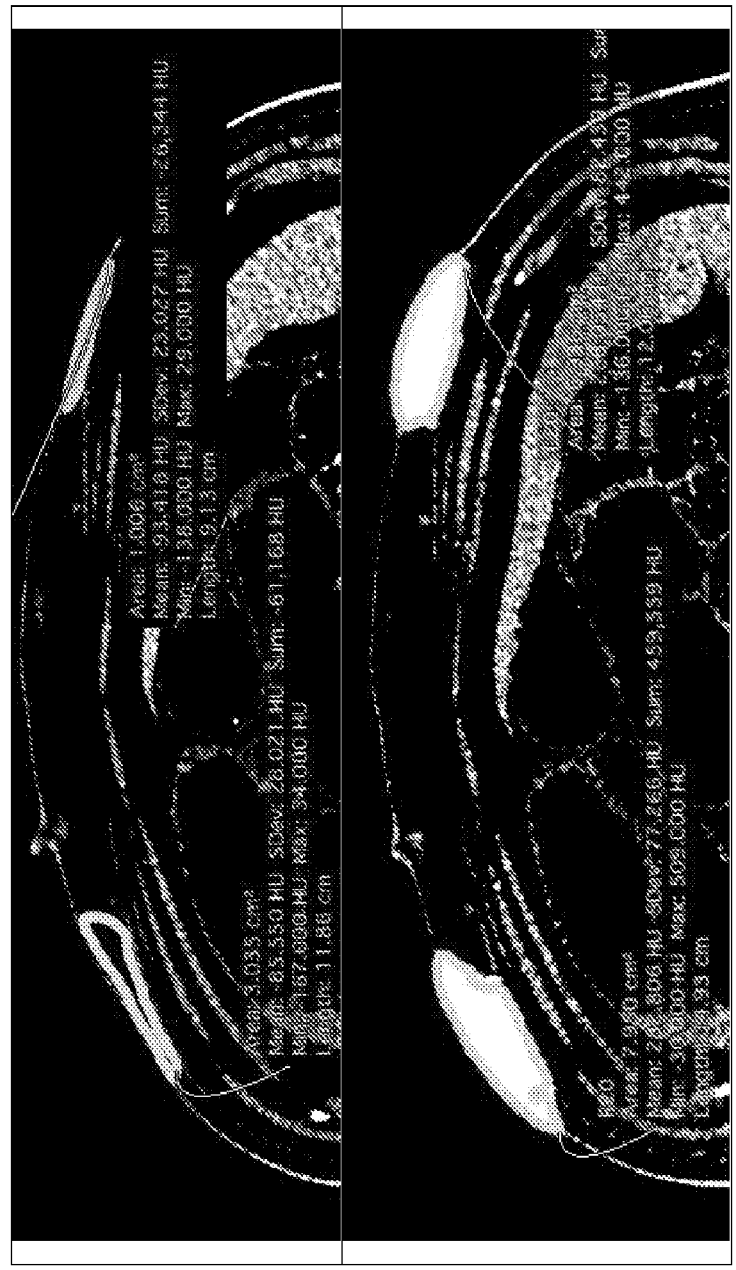
FIG. 14: Axial CT images before (top) and after (bottom) 20 mL tumescent injections. Green curves in bottom image outline the cross-section of the tumescence. Approximate outlines of the tissue before tumescence are shown in the top image. The mean attenuation is about −90 before injection and about 275 after injection. Measures of the tumescence evolution are shown in FIG. 15.

In a different experiment we took CT images roughly every 10 min instead of every hour in order to see the initially rapid dynamics. An axial cross-sectional image is shown in FIG. 14 before and after two 20 mL tumescent injections on symmetric sides of the anesthetized adult Yucatan pig's abdomen. The top image demonstrates that unexpanded subcutaneous tissue has an attenuation of about −90 HU, and the bottom image shows the same cross-section, after tumescence. The mean attenuation in the tumescence is about 270 mL, which corresponds to an average expansion of about 3×, consistent with the estimates from DW-MRI imaging (FIG. 10) and the direct thickness measurement in FIG. 2.

Figure 15:
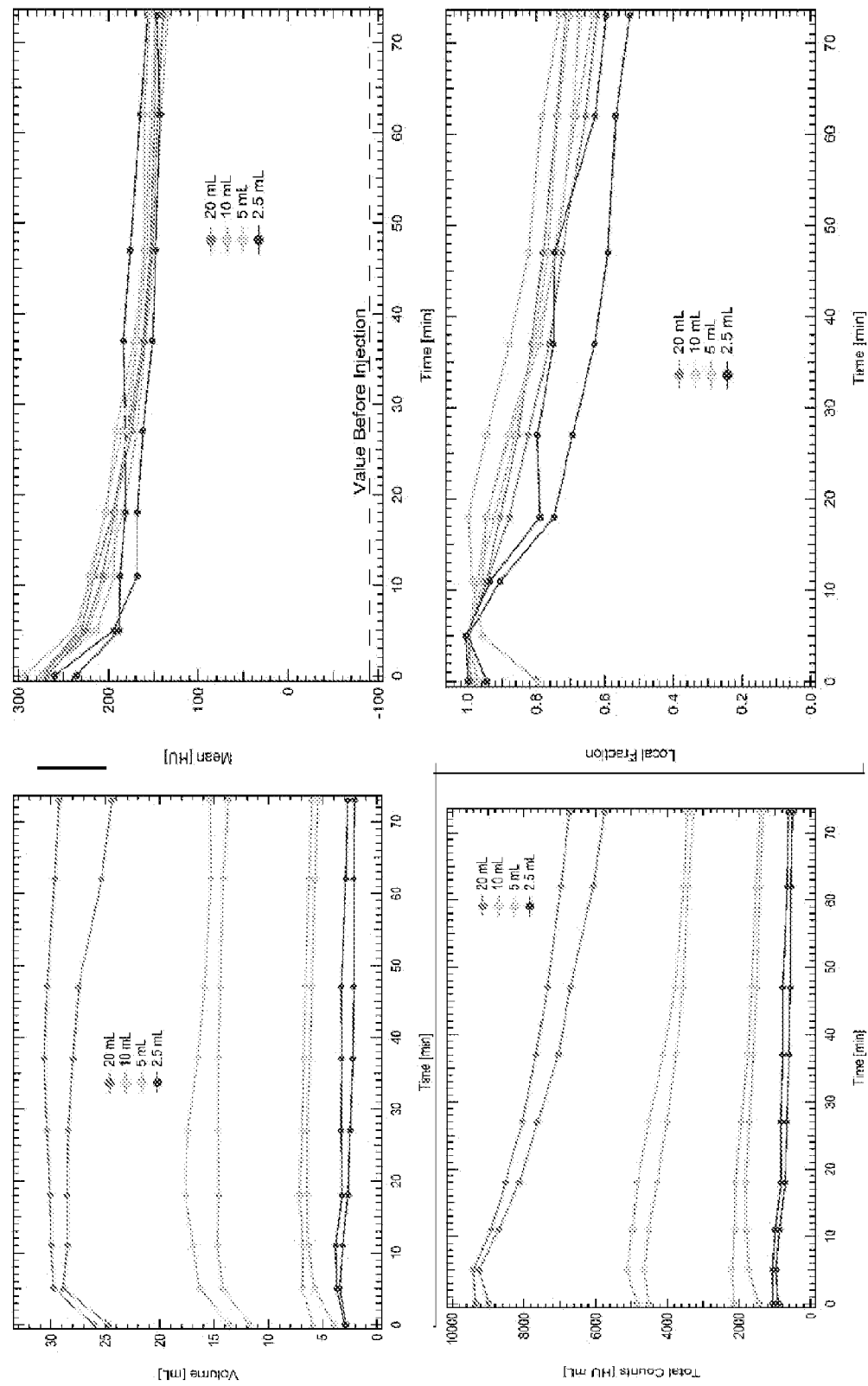
FIG. 15: The volume and mean attenuation of tumescent injections in to an adult Yucatan pig as they evolve over 70 min. Two injections of each volume were performed on symmetric sides of the abdomen as shown in FIG. 14. Total counts represents the volume multiplied by the mean, which is a measure of the total amount of contrast remaining in the tumescence. "Local Fraction" is the total counts curve normalized by its maximum.

FIG. 15 (top, left) shows the volume of tissue that has been infiltrated densely by the CT contrast agent over time. Note that there is an initial rise during the first 5 minutes, after which the volume stays constant. The initial rise is due to the spreading of the tumescent fluid after the completion of the injection into unexpanded tissue. The mean attenuation in the tumescent volume over time is shown in FIG. 15 (top, right). The initial, rapid drop is due to the spreading of fluid into unexpanded tissue—not absorption by lymph or capillaries—which decreases the mean attenuation over the tumescent volume. We verified this by multiplying the total volume and mean curves to get a measure of the "total contrast" that remains localized in the tumescence (FIG. 15 bottom, left). Dividing the total contrast curve by its maximum yields the "Localized Fraction" curves of FIG. 15 (bottom, right). We interpret the initially flat local fraction curve, with rising volume and dropping mean curves as localized spreading, which we have seen before occurs on short time scales. Over the 70 minutes of the experiment however, we see a ~30% drop in the local fraction, which we interpret as true take-up by lymph and capillaries. In other words, we have measured two timescale: 1) spontaneous spreading occurring in <5 minutes, and 2) take up by the serum ~1 hour.

An important question that arises is the length of time an antibiotic needs to act. There are two classes of antibiotics, bacteriostatic and bactericidal. Bactericidal antibiotics kill bacteria, whereas bacteriostatic antibiotics prevent them from reproducing, although the distinction is clinically arbitrary [64]. The minimum time a bacteriostatic drug would need to be effective is a few bacteria division times (doubling times). As division times are in the range of 20-50 min depending on the organism [65, 66], a few hours of high-concentration time are necessary. Our CT data shows that tumescent injections are capable of achieving sufficient residence time.

It should be emphasized that our observations are in healthy tissue, not infections, and that localization times might be affected by the different physiology surrounding wounds, especially chronic ones. The prolonged inflammatory state of chronic wounds changes the tissue properties. For example, fibrin is known to form "cuffs" around capillaries near venous ulcers [67] and is hypothesized to limit the flow of oxygen and nutrients. This "clogged" state could influence the residence time of any local infusion. Also, the expansion induced by a tumescent injection may open up clogged pores of chronically inflamed tissue and facilitate normal healing processes.

Health care professionals are confronted with the choice of how to treat a chronic wound on a continuous basis—yet rarely inject directly into the wound even when amputation is an immediate threat. This choice, which is made hundreds if not thousands of times per day, shows the need in the art for the new procedures for treating chronic wounds. As shown by the disclosure above, we have developed tumescent infusion procedures which can, for example, enhance hydraulic conductivity at surprisingly localized site(s) in vivo in order to disperse relatively high concentrations of antibiotic agents throughout tissue colonized by pathogenic organisms for a significant period of time (thereby providing new procedures for treating chronic wounds).

REFERENCES

This application references a number of different publications as indicated throughout the specification by reference numbers enclosed in brackets, e.g., [x]. A list of these different publications ordered according to these reference numbers can be found below.

[1] C. K. Sen, G. M. Gordillo, S. Roy, R. Kirsner, L. Lambert, T. K. Hunt, F. Gottrup, G. C. Gurtner and M. T. Longaker, "Human Skin Wounds: A Major and Snowballing Threat to Public Health and the Economy," *Wound Repair Regen*, vol. 17, no. 6, pp. 763-771, 2009.

[2] M. A. Fonder, G. S. Lazarus and D. A. Cowan, "Treating the chronic wound: A practical approach to the care of nonhealing wounds and wound care dressings," *Journal of the American Academy of Dermatology*, vol. 58, no. 2, pp. 185-206, 2008.

[3] I. K. Cohen, R. F. Diegelmann, D. R. Yager, I. L. Wornum III, M. F. Graham and M. C. Crossland, "Wound Care and Wound Healing," in *Principles of surgery*, New York, McGraw-Hill, 1999, pp. 263-295.

[4] K. G. Harding, H. L. Morris and G. K. Paten, "Healing chronic wounds," *British Medical Journal, International Edition*, vol. 324, no. 7330, pp. 160-163, 2002.

[5] P. Barua and B. K. Bhowmick, "Hypodermoclysis—a victim of historical prejudice," *Age and Aging*, vol. 34, pp. 215-217, 2005.

[6] G. Walsh, "Hypodermoclysis: An alternate method for rehydration in long-term care," *Journal of Infusion Nursing*, vol. 28, no. 2, pp. 123-129, 2005.

[7] M. Sasson and P. Shvartzman, "Hypodermoclysis: An alternative Infusion Technique," *American Family Physician*, vol. 64, no. 9, pp. 1575-1578, 2001.

[8] N. A. Hussain and G. Warshaw, "Utility of Clysis for Hydration in Nursing Home Residents," *Journal of the American Geriatrics Society*, vol. 44, no. 8, pp. 969-973, 1996.

[9] S. M. Gluck, "Hypodermoclysis Revisited," *Journal of the American Medical Association*, vol. 248, no. 11, pp. 1310-1311, 1982.

[10] E. Y. Berger, "Nutrition by Hypodermoclysis," *Journal of the American Geriatrics Society*, vol. 32, no. 3, pp. 199-203, 1984.

[11] R. G. Simpson, "Hyaluronidase in Geriatric Therapy," *Practitioner*, vol. 219, no. 1311, pp. 361-363, 1977.

[12] T. D. Day, "The permeability of interstitial connective tissue and the nature of the interfibrillary substance," *J. Physiol.*, vol. 117, pp. 1-8, 1952.

[13] O. Hechter, S. K. Dopkeen and M. H. Yudell, "The clinical use of hyaluronidase in hypodermoclysis," *The Journal of Pediatrics*, vol. 30, no. 6, pp. 645-656, 1947.

[14] W. Gaisford and D. G. Evans, "Hyaluronidase in Paediatric Therapy," *The Lancet*, vol. 2, no. 6577, pp. 505-507, 1949.

[15] O. Olsson and O. Lofgren, "Hyaluronidase as a factor hastening the spread and absorption of water-soluble radiopaque substances deposited intracutaneously, subcutaneously, or intramuscularly," *Acta Radiologica*, vol. 31, no. 3, pp. 250-256, 1949.

[16] F. Duran-Reynals, "The effects of extracts of certain organs from normal and immunized animals on the infecting power of vaccine virus," *Journal of*, vol. 50, no. 3, pp. 327-340, 1929.

[17] D. McClean, "Influence of testicular extract on dermal permeability and the response to vaccine virus," *Journal of Pathology and Bacteriology*, vol. 33, no. 4, pp. 1045-1070, 1930.

[18] F. Duran-Reynals, "Tissue permeability and the spreading factors in infection," *Bacteriology Reviews*, vol. 6, no. 4, pp. 197-252, 1942.

[19] A. C. Guyton, K. Scheel and D. Murphree, "Interstitial Fluid Pressure: III. Its Effect on Resistance to Tissue Fluid Mobility," *Circulation Research*, vol. 19, no. 2, pp. 412-419, 1966.

[20] A. C. Guyton, "Interstitial Fluid Pressure: II. Pressure-Volume Curves of Interstitial Space," Circulation Research, vol. 16, pp. 452-460, 1965.

[21] E. F. Azevedo, L. A. Barbosa and S. H. De Bortoli Cassiani, "Administration of antibiotics subcutaneously: and integrative literature review," *Acta Paulista de Enfermagem*, vol. 25, no. 5, pp. 817-822, 2012.

[22] G. Harb, F. Lebel, J. Battikha and J. W. Thackara, "Safety and pharmacokinetics of subcutaneous ceftriaxone administered with or without recombinant human hyaluronidase (rHuPH20) versus intravenous ceftriaxone administration in adult vulu," *Curr Med Res Opin.*, vol. 26, no. 2, pp. 279-88, 2010.

[23] N. Champoux, P. Du Souich, M. Ravaoarinoro, D. Phaneuf, J. Latour and J. R. Cusson, "Single-dose pharmacokinetics of ampicillin and tobramycin administered by hypodermoclysis in young and older healthy volunteers," *Br J Clin Pharmacol*, vol. 42, no. 3, pp. 325-31, 1996.

[24] K. Borner, H. Lode, B. Hampel, M. Pfeuffer and P. Koeppe, "Comparative Pharmacokinetics of Ceftriaxone after Subcutaneous and Intravenous Administration," *Chemotherapy*, vol. 31, no. 4, pp. 237-245, 1985.

[25] D. Frasca, S. Marchand, F. Petitpas, C. Dahyot-Fizelier, W. Couet and O. Mimoz, "Pharmacokinetics of Ertapenem following Intravenous and Subcutaneous Infusions in Patients," *Antimicrobial agents and Chemotherapy*, vol. 54, no. 2, pp. 924-926, 2010.

[26] J. Klein, "Tumescent Antibiotic Solution". U.S. Pat. No. 8,957,060 B2, 17 Feb. 2015.

[27] D. G. Warden and D. M. Heimbach, "Burns," in *Principles of surgery*, S. I. Schwartz, Ed., McGraw-Hill Health Professional Division, 1999, pp. 223-262.

[28] W. F. McManus, C. W. Goodwin Jr. and B. A. Pruitt Jr., "Subeschar Treatment of Burn-Wound Infection," *Arch Surg*, vol. 118, no. 3, pp. 291-4, 1983.

[29] C. R. Baxter, P. W. Curreri and J. A. Marvin, "The Control of Burn Wound Sepsis by the Use of Quantitative Bacteriologic Studies and Subeshar Clysis with Antibiotics," *Surgical Clinics of North America*, vol. 53, no. 6, pp. 1509-1518, 1973.

[30] L. C. D'Avignon, J. R. Saffle, K. K. Chung and L. C. Cancio, "Prevention and Management of Infections Associated with Burns in the Combat Casualty," *The Journal of Trauma Injury, Infection, and Critical Care*, vol. 64, no. 3, pp. S277-S286, 2008.

[31] R. Sinha, N. Sharma and R. Agarwal, "Subeschar clysis in deep burns," *Burns*, vol. 29, no. 8, pp. 854-6, 2003.

[32] W. F. McManus, A. D. Mason Jr. and B. A. Pruitt Jr., "Subeschar Antibiotic Infusion in the Treatment of Burn Wound Infection," *The Journal of Trauma*, vol. 20, no. 12, pp. 1021-1023, 1980.

[33] J. A. Klein, "The tumescent technique for Lipo-suction surgery," *The American Journal of Cosmetic Surgery*, vol. 4, pp. 263-267, 1987.

[34] J. A. Klein, Tumescent Technique: Tumescent Anesthesia & Microcannular Liposuction, St. Louis: Mosby, 2000.

[35] J. S. Glass, C. L. Hardy, N. M. Meeks and B. T. Carroll, "Acute pain management in dermatology: Risk assessment and treatment," *Journal of the American Academy of Dermatology*, vol. 73, no. 4, pp. 543-560, 2015.

[36] B. Sommer and G. Sattler, "Tumescent technique for local anesthesia. State of the art in dermatologic surgery," *Hautarzt*, vol. 49, no. 5, pp. 351-360, 1998.

[37] J. A. Klein, "Tumescent Technique for Regional Anesthesia Permits Lidocaine Doses of 35 mg/kg for Liposuction," *Journal of Dermatologic Surgery and Oncology*, vol. 16, no. 3, pp. 248-263, 1990.

[38] J. A. Klein, "Anesthetic Formulations of Tumescent Solutions," *Liposuction*, vol. 17, no. 4, pp. 751-759, 1999.

[39] J. H. Stewart, G. W. Cole and J. A. Klein, "Neutralized Lidocaine with Epinephrine for Local Anesthesia," *The Journal of Dermatologic Surgery and Oncology*, vol. 15, no. 10, pp. 1081-1088, 1989.

[40] J. H. Stewart, S. E. Chinn, G. W. Cole and J. A. Klein, "Neutralized Lidocaine with Epinephrine for Local Anesthesia—II," *The Journal of Dermatologic Surgery and Oncology*, vol. 16, no. 9, pp. 842-845, 1990.

[41] J. A. Klein, "Infiltration Cannula". U.S. Pat. No. 7,914,504 B2, 29 Mar. 2011.

[42] J. A. Klein, "The Tumescent Technique," *Liposuction*, vol. 8, no. 3, pp. 425-437, 1990.

[43] J. A. Klein, "Anesthesia for liposuction in dermatologic surgery," *Journal of dermatologic surgery and oncology*, vol. 14, no. 10, pp. 1124-1132, 1988.

[44] C. W. Hanke, S. Bullock and G. Bernstein, "Current Status of Tumescent Liposuction in the United States," *Dermatol Surg.*, vol. 22, no. 7, pp. 595-598, 1996.

[45] W. Hanke, S. E. Cox, N. Kuznets and W. P. Coleman III, "Tumescent Liposuction Report Performance Measurement Initiative: National Survey Results," *Dermatol. Surg.*, vol. 30, no. 7, pp. 967-978, 2004.

[46] I. J. Kucera, T. J. Lambert, J. A. Klein, R. G. Watkins, J. M. Hoover and A. D. Kaye, "Liposuction: contemporary issues for the anesthesiologist," *Journal of Clinical Anesthesia*, vol. 18, pp. 379-387, 2006.

[47] J. P. Rubin, C. Bierman, C. E. Rosow, G. R. Arthur, Y. Chang, E. H. Courtiss and J. W. May Jr., "The Tumescent Technique: The effect of high tissue pressure and dilute epinephrine on absorption of lidocaine," *Plastic and Reconstructive Surgery*, vol. 103, no. 3, pp. 990-996, 1999.

[48] B. N. Silberg, "System and Method of Vessel Removal". U.S. Pat. No. 6,565,521 B1, 20 May 2003.

[49] J. A. Klein, "Tumescent Antibiotic Delivery for Prevention of Surgical Site Infection," ClinicalTrials.gov, 26 Dec. 2014. [Online]. Available: https://clinicaltrials.gov/ct2/show/NCT02503904. [Accessed 2 Sep. 2016].

[50] B. N. Silberg, "Pre-surgical prophylactic administration of antibiotics and therapeutic agents". United States Patent Application Patent US 2010/0069827 A1, 18 Mar. 2010.

[51] B. N. Silberg, "Administration of antibiotics and therapeutic agents". U.S. Pat. No. 8,747,384 B2, 10 Jun. 2014.

[52] B. N. Silberg, "Administration of Antibiotics and Therapeutic Agents". United States Patent Application Patent US 2015/0258320 A1, 17 Sep. 2015.

[53] B. N. Silberg, "Ultrasonic Dispersion of Compositions in Tissue". United States Patent Application Patent US 2012/0123321 A1, 17 May 2012.

[54] B. N. Silberg, "Ultrasonic Dispersion of Compositions in Tissue". United States Patent Application Patent US 2015/0297879 A1, 22 Oct. 2015.

[55] B. Silberg, "External Ultrasound Treatment of Connective Tissue". U.S. Pat. No. 6,039,048, 21 Mar. 2000.

[56] B. N. Silberg, "Direct Antibiotic Delivery into Soft Tissue Infections Using Ultrasonic Dispersal," *Plastic and Reconstructive Surgery*, vol. 132, no. (4S-1), pp. 51-52, Octo 2016.

[57] Sonescence Inc., "Direct Antibiotic Delivery of Cefazolin Into Soft Tissue Infections Using Subcutaneous Injection and Ultrasonic Dispersion (DAD)," ClinicalTrials.gov, 8 Nov. 2010. [Online]. Available: https://clinicaltrials.gov/ct2/show/NCT01238276. [Accessed 2 Sep. 2016].

[58] S. D. Howkins, "Diffusion rates and the effect of ultrasound," *Ultrasonics*, vol. 7, no. 2, pp. 129-130, 1969.

[59] A. Tsukamoto, K. Tanaka, T. Kumata, K. Yoshida, Y. Watanabe, S. Miyata, K. S. Furukawa and T. Ushida, "1-MHz ultrasound enhances internal diffusivity in agarose gels," *Applied Acoustics*, vol. 73, no. 10, pp. 1117-1121, 2013.

[60] R. Nunan, K. Harding and P. Martin, "Clinical challenges of chronic wounds: searching for an optimal animal model to recapitulate their complexity," *Disease Models & Mechanisms*, vol. 7, no. 11, pp. 1205-1213, 2014.

[61] D. P. Nicolau and B. N. Silberg, "Assessing the Potency of Cefazolin against Methicillin-Resistant *Staphylococcus aureus* (MRSA): Microbiologic Data Supporting Ultrasonic Drug Dispersion for the Management of Skin & Skin Structure Infections (SSSIs). (Abstract No. C-1071)," in 55*th Interscience Conference on Antimicrobial Agents and Chemotherapy/International Congress of Chemotherapy and Infection*, San Diego, 2015.

[62] D.-M. Koh and D. J. Collins, "Diffusion-Weighted MRI in the Body: Applications and Challenges in Oncology," *American Journal of Roentgenology*, vol. 188, no. 6, pp. 1622-1635, 2007.

[63] M. Holz, S. R. Heil and A. Sacco, "Temperature-dependent self-diffusion coefficients of water and six selected molecular liquids for calibration in accurate 1H NMR PFG measurements," *Physical Chemistry Chemical Physics*, vol. 2, no. 20, pp. 4740-4742, 2000.

[64] G. A. Pankey and L. D. Sabath, "Clinical Relevance of Bacteriostatic versus Bactericidal Mechanisms of Action in the Treatment of Gram-Positive Bacterial Infections," *Clinical Infectious Diseases*, vol. 38, pp. 864-70, 2004.

[65] F. Laurent, H. Lelievre, M. Cornu, F. Vandenesch, G. Carret, J. Etienne and J.-P. Flandrois, "Fitness and competitive growth advantage of new gentamicin-susceptible MRSA clones spreading in French hospitals," *Journal of Antimicrobial Chemotherapy*, vol. 47, pp. 277-283, 2001.

[66] E. O. Powell, "An Outline of the Pattern of Bacterial Generation Times," *Microbiology*, vol. 18, pp. 382-417, 1958.

[67] N. L. Browse and K. G. Burnand, "The Cause of Venous Ulceration," *The Lancet*, vol. 320, no. 8292, pp. 243-245, 1982.

[68] U.S. National Institutes of Health, "Tumescent Antibiotic Delivery for Prevention of Surgical Site Infection," ClinicalTrials.gov, [Online]. Available: https://clinicaltrials.gov/ct2/show/NCT02503904.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A method of delivering an antibiotic agent to a chronic wound having a region of tissue colonized by a pathogenic microorganism, the method comprising:
   administering a solution comprising the antibiotic agent via tumescent injection to the region of colonized tissue, wherein:
   (a) the amount of solution administered is selected to be sufficient to expand the volume of the region of colonized tissue between 2 and 5-fold so as to create an edema on a skin surface that expands extracellular matrices throughout the colonized tissue;
   (b) the antibiotic solution is administered so that the concentration of the antibiotic agent within the tissue that has been expanded is above a minimum inhibitory concentration for the pathogenic microorganism for at least 4 hours;
   (c) the antibiotic solution is administered so as to generate a hydraulic conductivity throughout the colonized tissue that is at least 10 times greater than the hydraulic conductivity in tissue that has not been expanded;
   (d) the antibiotic solution is administered at a rate selected to form an observable boundary between the tissue that has been expanded and the tissue that has not been expanded; and
   (e) the administration of the antibiotic solution is monitored so that the observable boundary occurs in uncolonized tissue and is at least 1 centimeter away on the skin surface from the region of colonized tissue.

2. The method of claim 1, wherein the method is performed in the absence of the application of a vasoconstrictor to the colonized tissue.

3. The method of claim 2, wherein the method is performed in the absence of the application of mechanical stimulation to the colonized tissue.

4. The method of claim 3, wherein the amount of solution administered is selected to generate an apparent diffusion coefficient throughout the tissue that has been expanded that is greater than 90% of the value for bulk water ($2.5 \times 10^{-3}$ mm$^2$ s$^{-1}$ at 40 C).

5. The method of claim 4, wherein the antibiotic solution is administered so that the concentration of the antibiotic agent within the tissue that has been expanded is at least 2, 4 or 6 times a minimum inhibitory concentration for the pathogenic microorganism for at least 4 hours.

6. The method of claim 5, wherein the pathogenic microorganism is resistant to antibiotic agents administered systemically.

7. The method of claim 1, wherein the boundary is observed by the naked eye and at least one further technique selected from 3-D scanning, computed tomography (CT), diffusion-weighted magnetic resonance imaging (DW-MRI), and poroviscoelastic relaxation.

8. The method of claim 1, wherein the antibiotic solution is administered in a plurality of infusions so that the concentration of the antibiotic agent within the tissue that has been expanded is above a minimum inhibitory concentration for the pathogenic microorganism for at least 4 hours.

9. The method of claim 1, wherein the chronic wound is a venous ulcer, an arterial ulcer, a diabetic ulcer, or a pressure ulcer.

10. A method of delivering an antibiotic agent to a chronic wound having a region of tissue colonized by a pathogenic microorganism, the method comprising:
   administering a solution comprising the antibiotic agent via tumescent injection to the region of colonized tissue, wherein the volume of the solution is selected and monitored so that:
   (a) the volume of antibiotic solution administered is sufficient to expand the area of the colonized tissue between 2 and 5-fold so as to create an edema on a skin surface that expands extracellular matrices of colonized tissue throughout the colonized tissue;
   (b) the antibiotic solution is administered in a manner selected to generate:
      an apparent diffusion coefficient at that is greater than 90% of the value for bulk water ($2.5 \times 10^{-3}$ mm$^2$ s$^{-1}$ at 40 C) throughout the tissue that has been expanded; and
      a boundary between the tissue that has been expanded and the tissue that has not been expanded; wherein:
      the boundary is located at a region where the hydraulic conductivity changes at least one order of magnitude between the tissue that has been expanded and the tissue that has not been expanded; and
      the administration of the antibiotic solution is monitored so that the boundary occurs in uncolonized tissue and is at least 1 centimeter away on the skin surface from the region of colonized tissue.

11. The method of claim 10, wherein the method includes the step of debriding the chronic wound within 24 hours prior to delivering the antibiotic agent to the chronic wound.

12. The method of claim 11, further comprising grafting skin at the site of the chronic wound within 24 hours following delivering the antibiotic agent to the chronic wound.

13. The method of claim 12, wherein the method is performed in the absence of the application of a vasoconstrictor to the colonized tissue.

14. The method of claim 13, wherein the tumescent injection is performed in a manner that avoids application of mechanical stimulation to the colonized tissue.

15. A method of treating a chronic wound colonized by a pathogenic microorganism comprising:
   (a) debriding the wound to remove non-viable tissue and expose a layer of granulation tissue;
   (b) delivering an antibiotic agent to regions of colonized tissue in the chronic wound, the method comprising:
      (i) administering a solution comprising the antibiotic agent via tumescent injection to the regions of colonized tissue, wherein:
      (ii) the amount of solution administered is selected to be sufficient to expand the volume of the regions of colonized tissue between 2 and 5-fold so as to create an edema on a skin surface that expands extracellular matrices throughout the colonized tissue;
      (iii) the antibiotic solution is administered so that the concentration of the antibiotic agent within the tissue that has been expanded is above a minimum inhibitory concentration for the pathogenic microorganism for at least 4 hours;
      (iv) the antibiotic solution is administered so as to generate a hydraulic conductivity throughout the colonized tissue that is at least 10 times greater than the hydraulic conductivity in tissue that has not been expanded;
      (v) the antibiotic solution is administered at a rate selected to form an observable boundary between the tissue that has been expanded and the tissue that has not been expanded; and
      (vi) the administration of the antibiotic solution is monitored so that the observable boundary occurs in uncolonized tissue and is at least 1 centimeter away on the skin surface from the region of colonized tissue; and
   (c) applying a skin graft to the debrided tissue following tumescent injection of the antibiotic agent.

16. The method of claim 15, wherein the method is performed in the absence of the application of a vasoconstrictor to the colonized tissue.

17. The method of claim 15, wherein the tumescent injection is performed in a manner that avoids application of mechanical stimulation to the tissue expanded by the antibiotic solution.

18. The method of claim 15, wherein the boundary is observed by the naked eye and at least one further technique selected from 3-D scanning, computed tomography (CT), diffusion-weighted magnetic resonance imaging (DW-MRI), and poroviscoelastic relaxation.

19. The method of claim 18, wherein the solution is formulated to include an imaging agent that facilitates observation of the area of colonized tissue that has been expanded between 2 and 5-fold.

20. The method of claim 15, wherein the chronic wound is a venous ulcer, an arterial ulcer, a diabetic foot ulcer, or a pressure ulcer.

* * * * *